(12) United States Patent
Lentz

(10) Patent No.: US 8,657,845 B2
(45) Date of Patent: Feb. 25, 2014

(54) MULTIFILAR CABLE CATHETER

(75) Inventor: David Christian Lentz, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 915 days.

(21) Appl. No.: 11/748,906

(22) Filed: May 15, 2007

(65) Prior Publication Data
US 2008/0287786 A1    Nov. 20, 2008

(51) Int. Cl.
*A61M 29/00*    (2006.01)

(52) U.S. Cl.
USPC .......................................................... 606/194

(58) Field of Classification Search
USPC ............. 606/108, 192, 194; 604/103.04, 509; 623/1.11
See application file for complete search history.

(56) References Cited

U.S. PATENT DOCUMENTS

| | | | |
|---|---|---|---|
| 4,362,150 A | 12/1982 | Lombardi, Jr. et al. |
| 4,660,571 A | 4/1987 | Hess et al. |
| 4,762,129 A | 8/1988 | Bonzel |
| 4,906,241 A | 3/1990 | Noddin et al. |
| 4,917,104 A | 4/1990 | Rebell |
| 4,960,410 A | 10/1990 | Pinchuk |
| 4,976,720 A | 12/1990 | Machold et al. |
| 4,998,923 A | 3/1991 | Samson et al. |
| 5,295,962 A | 3/1994 | Crocker et al. |
| 5,324,259 A | 6/1994 | Taylor et al. |
| 5,346,505 A | 9/1994 | Leopold |
| 5,425,711 A | 6/1995 | Ressemann et al. |
| 5,429,597 A | 7/1995 | Demello et al. |
| 5,507,768 A | 4/1996 | Lau et al. |
| 5,507,995 A | 4/1996 | Schweich, Jr. et al. |
| 5,533,968 A | 7/1996 | Muni et al. |
| 5,613,948 A | 3/1997 | Avellanet |
| 5,643,278 A | 7/1997 | Wijay et al. |
| 5,690,644 A | 11/1997 | Yurek et al. |
| 5,695,468 A | 12/1997 | Lafontaine et al. |
| 5,711,909 A | 1/1998 | Gore et al. |
| 5,728,067 A | 3/1998 | Enger |
| 5,810,867 A * | 9/1998 | Zarbatany et al. ............ 606/191 |
| 5,906,606 A | 5/1999 | Chee et al. |
| 5,932,035 A | 8/1999 | Koger et al. |
| 5,938,587 A | 8/1999 | Taylor et al. |
| 5,941,869 A | 8/1999 | Patterson et al. |
| 5,980,486 A * | 11/1999 | Enger ...................... 604/103.04 |

(Continued)

FOREIGN PATENT DOCUMENTS

| | | |
|---|---|---|
| EP | 1 374 943 A1 | 1/2004 |
| JP | 2002/275774 | 9/2002 |

(Continued)

OTHER PUBLICATIONS

English translation of JP 2003-250898 (Miki et al., Sep. 2003).*

(Continued)

*Primary Examiner* — Katherine Dowe
(74) *Attorney, Agent, or Firm* — Brinks Gilson & Lione

(57) ABSTRACT

A balloon catheter device of the present invention includes an elongate catheter shaft comprising multifilar cable tubing having a proximal portion and a distal portion. The proximal portion includes a coating that allows the shaft to provide a patent fluid passage, and a part of the distal portion inside a balloon may be uncoated or otherwise open to the balloon lumen, allowing for passage of fluid through the shaft into the balloon lumen.

22 Claims, 20 Drawing Sheets

(56) References Cited

U.S. PATENT DOCUMENTS

| | | | |
|---|---|---|---|
| 6,030,405 A | 2/2000 | Zarbatany et al. | |
| 6,102,890 A | 8/2000 | Stivland et al. | |
| 6,107,004 A | 8/2000 | Donadio, III | |
| 6,186,978 B1 | 2/2001 | Samson et al. | |
| 6,278,057 B1 | 8/2001 | Avellanet | |
| 6,346,092 B1 | 2/2002 | Leschinsky | |
| 6,548,010 B1 | 4/2003 | Stivland et al. | |
| 6,589,227 B2 | 7/2003 | Sønderskov Klint | |
| 6,629,952 B1 | 10/2003 | Chien et al. | |
| 6,648,854 B1 | 11/2003 | Patterson et al. | |
| 6,692,460 B1 | 2/2004 | Jayaraman | |
| 6,755,855 B2 | 6/2004 | Yurek et al. | |
| 7,025,758 B2 | 4/2006 | Klint | |
| 7,037,291 B2 | 5/2006 | Lee et al. | |
| 7,117,703 B2 | 10/2006 | Kato et al. | |
| 7,306,585 B2 | 12/2007 | Ross | |
| 2001/0029362 A1* | 10/2001 | Sirhan et al. | 604/524 |
| 2003/0105427 A1* | 6/2003 | Lee et al. | 604/103.04 |
| 2004/0010243 A1* | 1/2004 | Klint | 604/526 |
| 2004/0092867 A1* | 5/2004 | Murray, III | 604/103 |
| 2004/0133158 A1 | 7/2004 | Keith et al. | |
| 2005/0245962 A1* | 11/2005 | Adams et al. | 606/194 |
| 2005/0283221 A1 | 12/2005 | Mann et al. | |
| 2006/0259118 A1 | 11/2006 | Pal et al. | |
| 2007/0208350 A1* | 9/2007 | Gunderson | 606/108 |
| 2008/0097398 A1* | 4/2008 | Mitelberg et al. | 604/525 |

FOREIGN PATENT DOCUMENTS

| | | |
|---|---|---|
| JP | 2003-250898 | 9/2003 |
| WO | WO 93/04722 | 3/1993 |
| WO | WO 98/44981 | 10/1998 |
| WO | WO 2006/107919 | 10/2006 |

OTHER PUBLICATIONS

Creganna Medical Devices brochure, 2004, 14 pages.
International Search Report and Written Opinion from related PCT Application No. PCT/US2005/0045282, Dec. 14, 2005.
International Search Report and Written Opinion from related PCT Application No. PCT/US2006/012424, filed Apr. 4, 2006.
Meredith, Ian T., Driver™ Stent Experience, Dec. 2003, 18 pages.

* cited by examiner

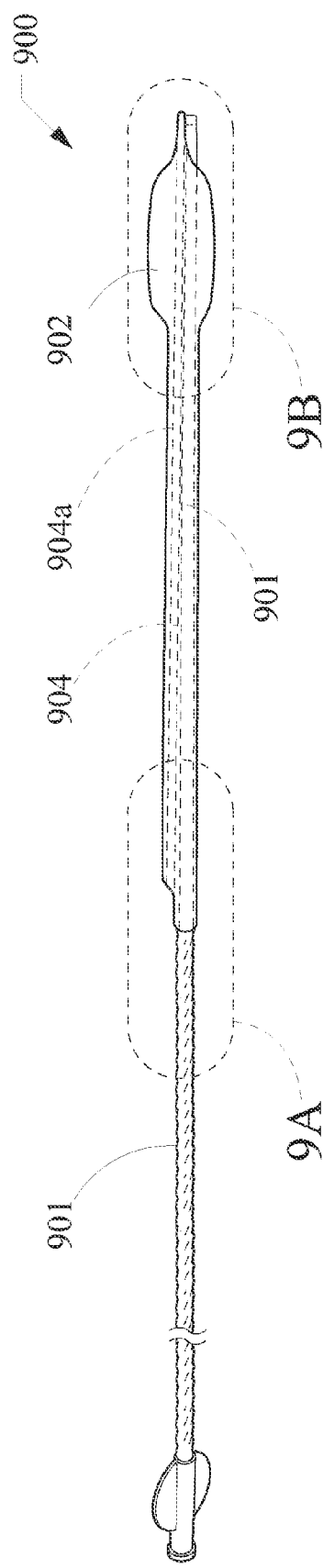
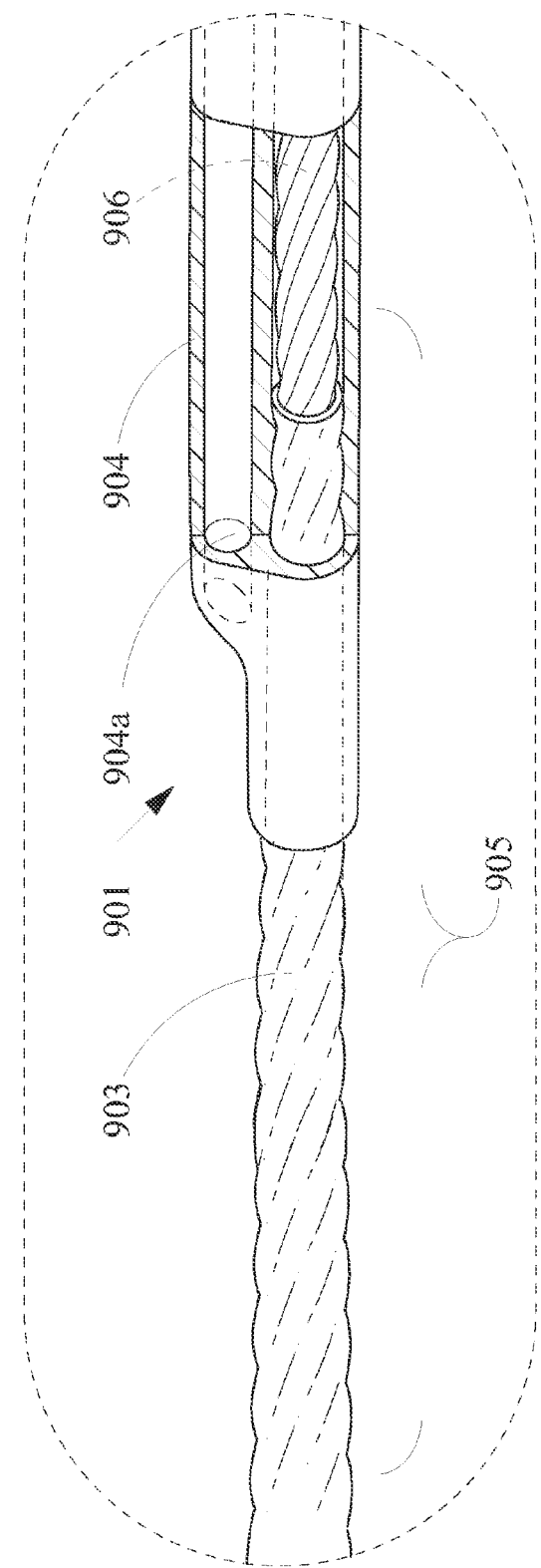
Fig. 9
Fig. 9A

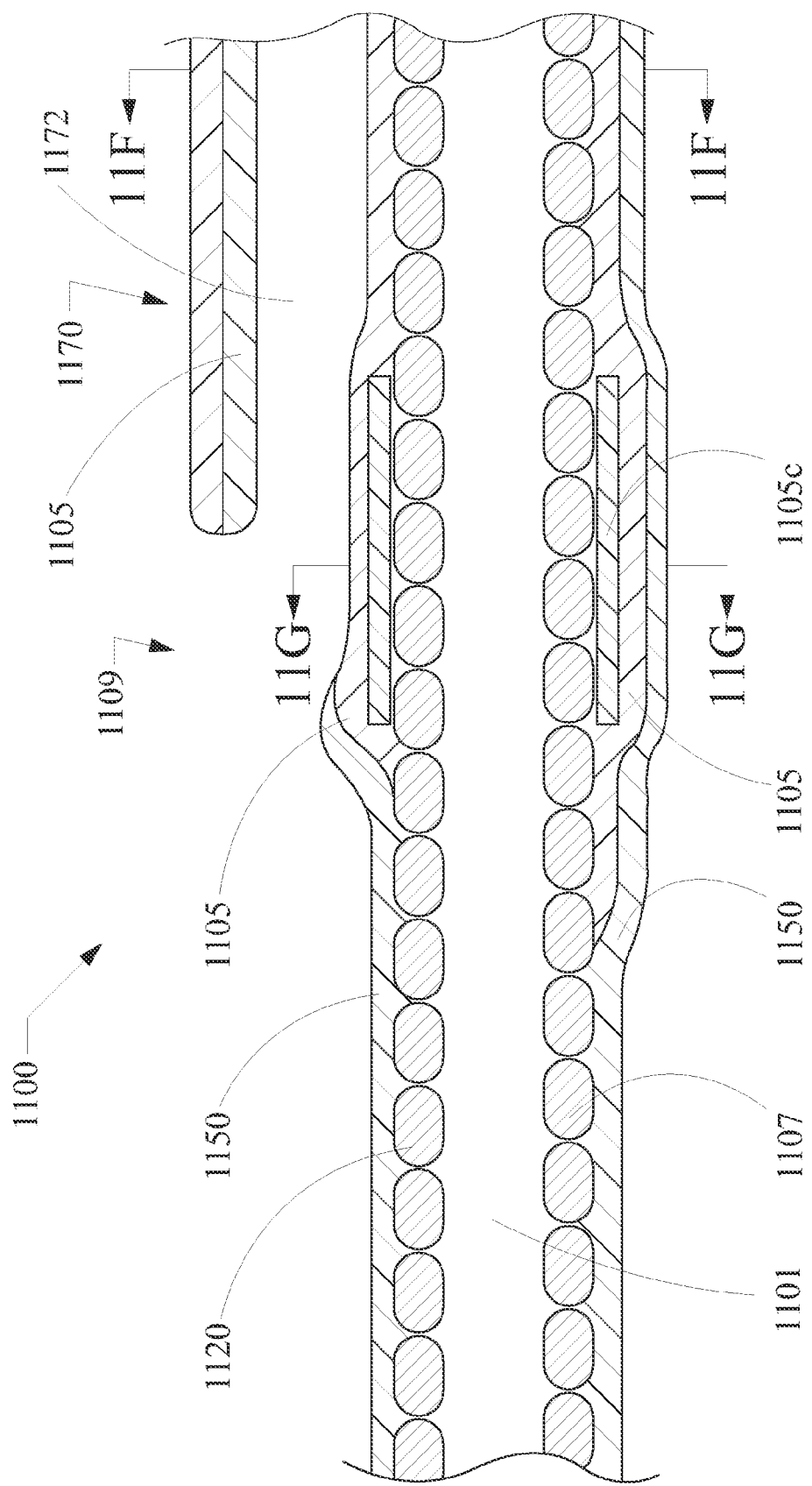

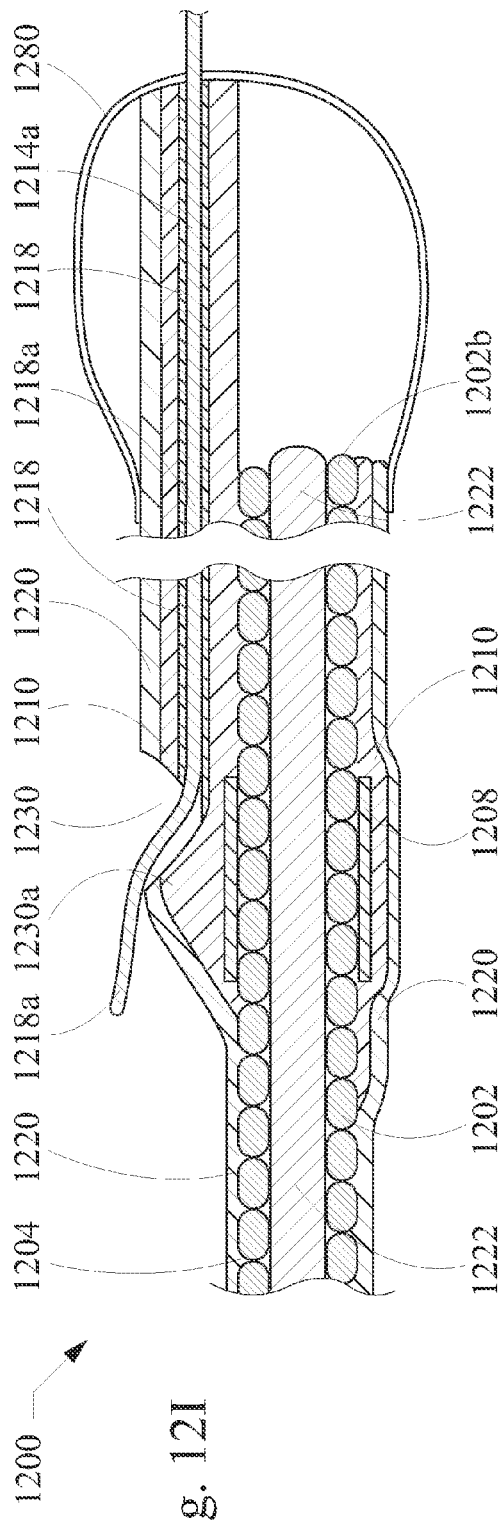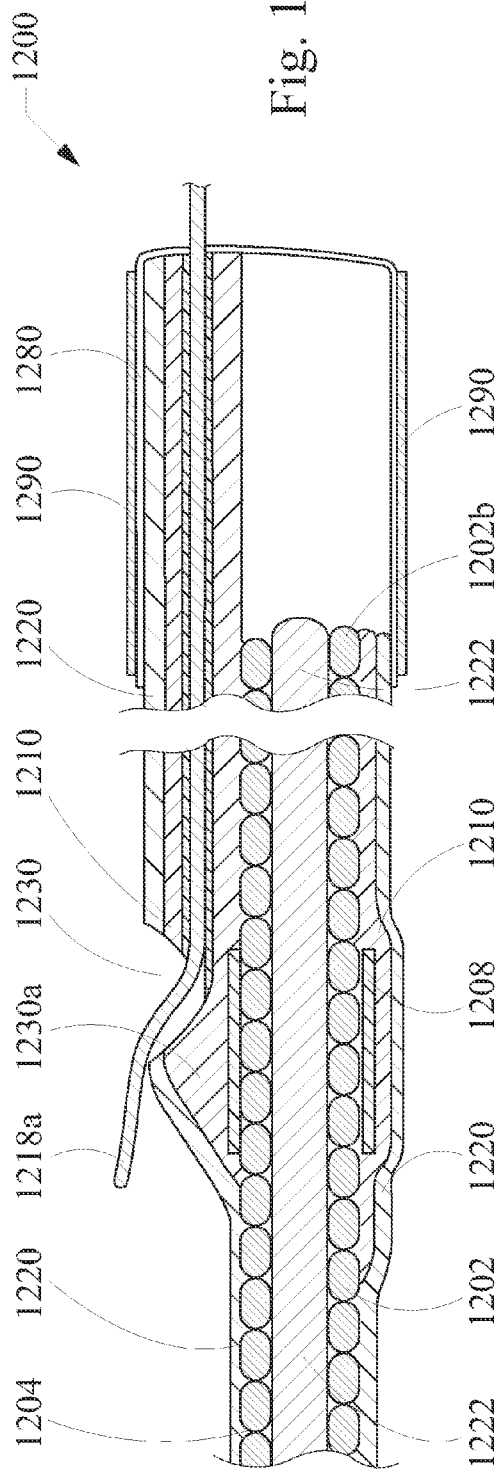

MULTIFILAR CABLE CATHETER

TECHNICAL FIELD

The present application relates to medical catheters, and more specifically to medical catheters useful in endovascular and other body lumens.

BACKGROUND

Medical delivery catheters are well known in the art of minimally invasive surgery for introduction of fluids and devices to sites inside a patient's body. For example, balloon dilation of luminal stenoses (e.g., in procedures such as angioplasty or balloon dilation of a bile duct), stent placement, and introduction of radio-opaque contrast fluids are common uses of catheters.

The most widely used form of angioplasty makes use of a dilation catheter having an inflatable balloon at its distal end. In coronary procedures, a hollow guide catheter or wire guide typically is used for guiding the dilation catheter through the vascular system to a position near the stenosis (e.g., to a coronary arterial lumen occluded by plaque). Using fluoroscopy, the physician guides the dilation catheter the remaining distance through the vascular system until a balloon is positioned to cross the stenosis. The balloon is then inflated by supplying pressurized fluid, through an inflation lumen in the catheter, to the balloon. Inflation of the balloon causes a widening of the lumen of the artery to reestablish acceptable blood flow through the artery. In some cases, a stent may be deployed with or instead of the balloon to widen and hold open the occluded arterial lumen.

Preferably a catheter used in endovascular lumens will have several physical characteristics. The profile and shaft size of the dilation catheter should be such that the catheter can reach and cross a very tight stenosis. Portions of the dilation catheter must also be sufficiently flexible to pass through a tight curvature or tortuous passageway, especially in a catheter adapted for use in the coronary arteries. The ability of a catheter to bend and advance effectively through the endovascular or other lumens is commonly referred to as the "trackability of the catheter." Another important feature of a dilation catheter is its "pushability." Pushability involves the transmission of longitudinal forces along the catheter from its proximal end to its distal end so that a physician can push the catheter through the vascular or other lumenal system and the stenoses. Effective catheters should be both trackable and pushable.

Two commonly used types of dilation catheters are referred to as "long-wire" catheters and "short-wire" catheters. A long-wire catheter is one in which a wire guide lumen is provided through the length of the catheter that is adapted for use with a wire guide that can first be used to establish the path to and through a stenosis to be dilated. The dilation catheter can then be advanced over the wire guide until the balloon on the catheter is positioned within the stenosis.

In short-wire catheters, the wire guide lumen may not extend the entire length of the catheter. In this type of catheter, the wire guide lumen may extend only from the distal end of the balloon to a point intermediate the distal and proximal ends of the catheter. This shorter lumen is the only portion of the catheter contacting the wire guide. It is sometimes desirable to exchange this first catheter and/or balloon for a second catheter (e.g., to "exchange out" a balloon catheter, and then "exchange in" a stent-deployment catheter). The exchange is preferably executed by leaving the wire guide in place during removal of the first catheter and using it as a guide for the second catheter. The first catheter is withdrawn or otherwise removed over the wire guide, and then a second catheter is introduced over the wire guide.

Short-wire catheters are often easier to exchange than catheters having the wire guide lumen extending the entire length of the catheter. This is because the wire guide need not be as long as a "long wire" configuration, which requires that a length of the wire guide extending outside the patient's body be longer than the portion of the catheter extending over the long wire guide in order for a doctor or assistant to maintain a grasp on the wire guide (to avoid undesired movement or displacement thereof). The short wire guide configuration catheters also create less friction during mounting and exchange operations due to the shorter wire guide lumen, leading to a reduced likelihood of displacing the wire guide.

Catheters for use in endovascular lumens typically require a variation in physical properties along different portions thereof. For example, a certain degree of stiffness is required for pushability and trackability near the proximal end while distal end requires a great deal of flexibility. A catheter having uniform properties throughout its length poses disadvantages in that it is likely to be too proximally flexible or too distally stiff. As a result, most catheter shafts (especially endovascular catheters) are made from multiple materials along the shaft length. For example, a catheter shaft may have a stiff proximal portion made of metal hypotube, a middle portion made of a stiff plastic, and a distal portion made of a more flexible plastic. This combination of materials poses problems of cost and efficiency in construction, and the junctions provide problematic possibilities for structural failure (such as binding, kinking, or even separation) as well as requiring specialized connection means. In another example, a catheter shaft may be made of plastic for a major part of its length, but have a stiffening wire disposed through a significant portion of that length to enhance stiffness. Some long wire catheters rely almost wholly on placement of a wire guide therethrough to retain the needed stiffness, which presents the problems of length and unwieldiness discussed above. In contrast, the proximal sections of short wire catheters must have adequate stiffness independent of the wire guide.

Several different structures for shortened guide wire lumen dilation catheters have been proposed and used to obtain the desired physical properties described above, but each of these structures tends to suffer from several disadvantages. For example, in a short wire catheter having a relatively flexible one-piece plastic design, because only a small portion of the wire guide extends through the catheter body near the distal end of the catheter shaft, the wire guide portion does not contribute to the pushability of the rest of the catheter shaft. As a result, the proximal shaft portion of such a catheter has low column strength. With such a configuration, the shafts and guide wire may tend to develop undesirable flexure (e.g., scissoring, bowing, buckling, kinking) when the balloon is being manipulated in a lumen. This undesired flexure may cause an irregular exterior surface such as a sharp edge which can in turn cause injurious abrasions to the inner lining of the artery or other lumen (e.g. other body lumen or a working lumen of an endoscope). This undesired flexure also leads to poor pushability and trackability of the catheter. To counteract this deficiency, some known designs have extended the length of the wire guide lumen and/or provided additional stiffener elements in the shaft.

In one design, a significant proximal portion of the catheter shaft is made of a metallic tubing (commonly referred to as a hypotube), which provides the desired pushability while maintaining a relatively small outer diameter. The distal portion of the catheter shaft is a second, more flexible (commonly plastic) tubing. In short-wire catheters using the hypotube design, a first aperture for introduction of a wire guide to the wire guide lumen is usually placed in the hypotube near to the distal end thereof. Alternatively, this first aperture is placed in the second tubing, or near the juncture between the hypotube and second tubing. These types of catheters, however, present certain disadvantages. Having the first aperture in the hypotube mitigates the advantages of a short-wire catheter: the wire guide must be longer, and advantages conferred by reduced friction are lessened. Having the first aperture at the aforementioned junction or in the second tubing creates a likelihood of undesired flexure (e.g., kinking or bunching) as there will be at least some portion of the more flexible second tubing unsupported by a wire guide, and therefore lacking column strength. Not only may such undesired flexure injure an endovascular or other lumen housing the catheter, but it may close off an inflation lumen or other lumen of the catheter, which is undesirable. The problems of increased cost of assembly and various mechanical problems presented by constructing and using a catheter having both semi-flexible hypotube and more flexible second tubing portions of the same catheter are addressed in the present invention.

BRIEF SUMMARY

In one aspect the present invention provides a catheter device, adaptable for use in endovascular lumens or other body lumens, that has a construction of multifilar cable tubing for a substantial portion of its length and that is adaptable for use in a short-wire or long-wire configuration. The embodiments described and claimed herein provide a multifilar catheter shaft having good pushability and trackability. Embodiments of the present invention may be adaptable for a variety of applications (e.g., placement of expandable stents, balloon dilation of stenoses) and use in a variety of surgical locations (e.g., vascular, gastroenterological).

The embodiments herein may be adaptable for use in a variety of minimally invasive surgical treatments (including, e.g., angioplasty or bile duct dilation).

BRIEF DESCRIPTION OF THE DRAWINGS

FIGS. 11A-11B are detail views of FIG. 11;

FIGS. 12A-12K show one method of making a catheter of the present invention.

DETAILED DESCRIPTION

In one aspect, presently described embodiments of a multifilar tube catheter shaft may be adaptable for use in a variety of minimally invasive surgical applications (e.g. endoscopic procedures, central or peripheral cardiovascular intervention procedures such as, for example, angioplasty).

Figure 1:
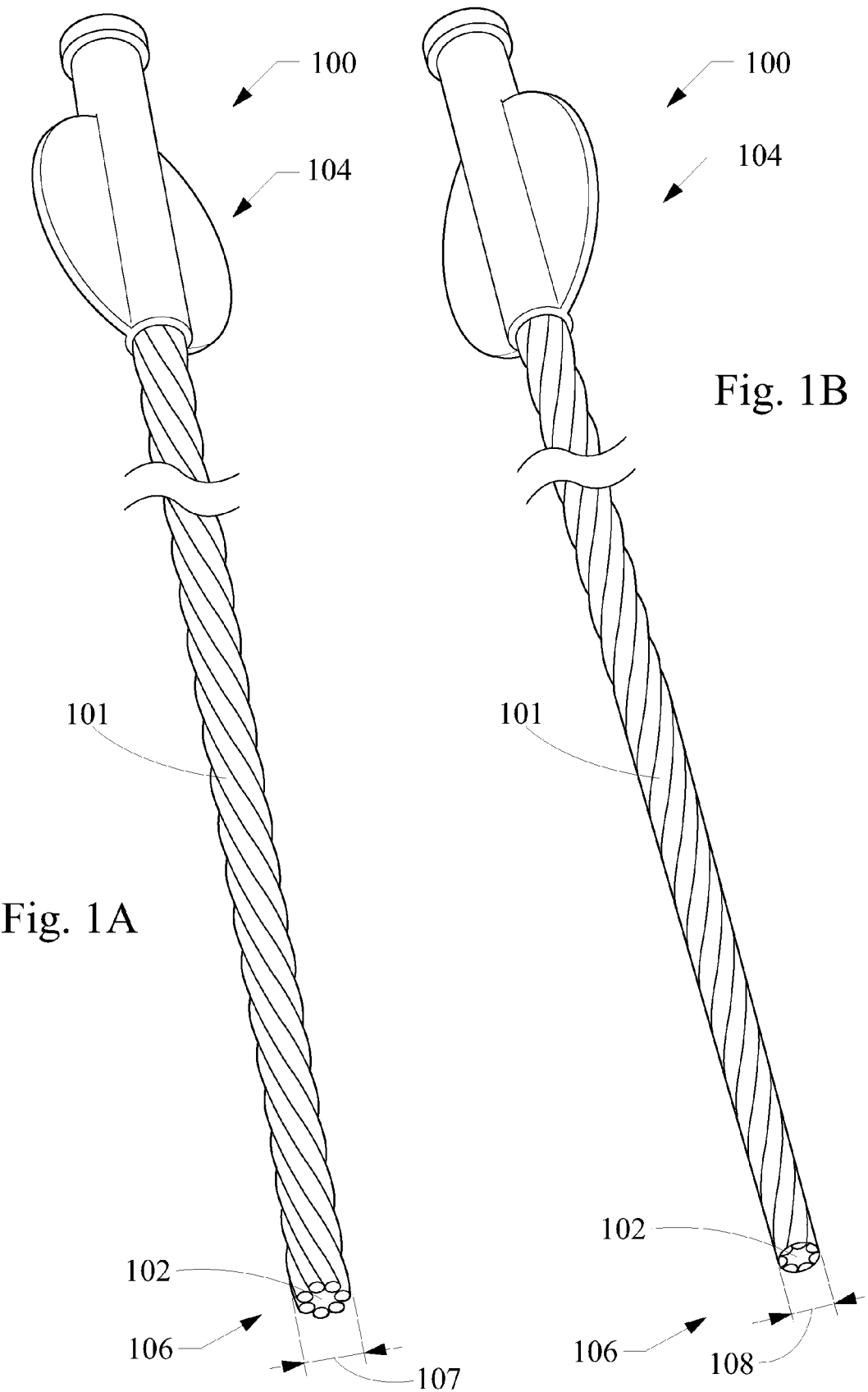
FIG. 1A is a perspective view of a catheter, with an enlarged detail view of the catheter's distal end.
FIG. 1B is a perspective view of a tapered catheter device, with an enlarged detail view of the catheter's distal end.

FIGS. 1A-1B illustrate an embodiment of a catheter device 100 with a shaft 101 constructed of a multifilar material and having an internal lumen 102. The multifilar tubing described is made of a plurality of wires twisted together and leaving a central lumen. Such multifilar tubing may be obtained, for example, from Asahi-Intecc (Newport Beach, Calif.). Materials and methods of manufacturing suitable multifilar tubing are described in Published U.S. Pat. No. 7,117,703 (Kato et al.), the contents of which are incorporated herein by reference. Use of multifilar tubing in a vascular catheter device is described in U.S. Pat. No. 6,589,227 (Sonderskov Klint, et al.; Assigned to Cook Inc. of Bloomington, Ind. and William Cook Europe of Bjaeverskov, Denmark), which is also incorporated herein by reference. As illustrated in the embodiments shown herein, the preferred multifilar tubing of the present invention is a monolayer multifilament tubing, which includes a single columnar layer of generally longitudinally_parallel filars and is distinguished from crosswound multifilar tubing or braided tubing known and used in the art. Described another way, a preferred multifilar tubing of the present invention includes a wire-stranded hollow coil body, which includes a plurality of coil line elements stranded along a predetermined circular line to form a flexible linear tube having a central axial hollow portion forming a lumen. In addition, the preferred multifilar tubing of the present invention is distinguished from multifilar wire guides as having a fluid-patent lumen configured for efficient fluid communication (e.g., of pressurized inflation fluid). The preferred monolayer multifilar tubing provides very desirable pushability and trackability with virtually no probability of kinking. The monolayer tubing may include interior or exterior coatings.

In FIG. 1A, the exterior diameter 107 is approximately the same along the length of the shaft 101. In the embodiment shown in FIG. 1B, the proximal end 104 has a greater exterior diameter than the distal end 106. The catheter shaft 101 tapers toward a smaller exterior diameter 108 at the distal end 106. Tapering can enhance flexibility of the shaft 101 in several ways. For example, flexibility is enhanced by decreasing the outside diameter of the catheter shaft 101. The portion of the catheter shaft 101 having a smaller diameter is more flexible than the portion having a larger diameter. Such tapering also decreases the thickness of the wall of the catheter shaft 101. Alternatively, tapering may be used within the internal diameter of a catheter, enhancing flexibility by decreasing wall thickness without altering the exterior diameter of the shaft 101. The steepness and location of the tapering is determined by the desired application for the catheter shaft 101. For example, in alternative embodiments, there may be multiple stepwise or gradual differences in diameter to confer different degrees of flexibility throughout the length of the catheter. For example, catheter shaft 101 for use in coronary arteries will typically benefit from a smaller diameter than a catheter shaft 101 for use in a bile duct, both for gross size and flexibility. A grinding process or other suitable process may be used to reduce the exterior diameter as appropriate for the desired application. Reducing the exterior diameter provides an added benefit by reducing the profile of the device. The flexibility of the catheter shaft 101 or a portion thereof may also be altered by increasing or decreasing the number of filars. In one aspect, the embodiments described herein also provide a catheter shaft having consistent construction material throughout most of the length of the catheter shaft, with gradual transition from a stiffer proximal end to a more flexible distal end and lacking sharp transitions that undermine structural integrity.

A further embodiment of the catheter shaft 101 includes a coating on internal and/or external surfaces for at least a portion of the catheter shaft 101. The coating is selected to confer or improve one or more properties of reduced friction, flexibility, and sealing a lumen 102 of the catheter. Sealing the lumen 102 allows the lumen to be used, for example, for introduction of inflation fluid to a dilation balloon or introduction of a medicative substance or radio-opaque contrast fluid.

Figure 2:
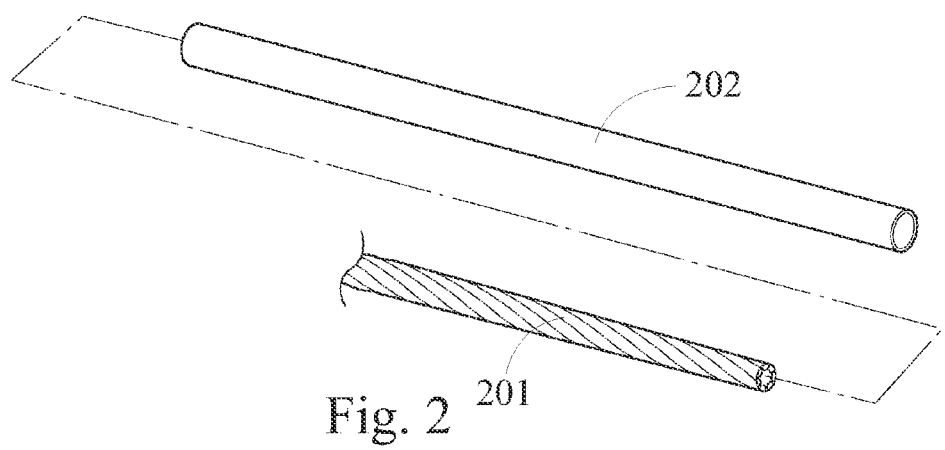
FIG. 2 is a perspective view of a catheter shaft with a sleeve.

The coating may be, for example, a sheath or sleeve 202 as illustrated in FIG. 2. In various alternative embodiments, the sheath 202 may comprise an extruded sleeve, shrink tube, extruded over-jacket, or dip coat. The sheath 202 is preferably a thermoset material or a thermoplastic material and may comprise, for example, HDPE, PTFE, PET, polyester or polyether block amide (PEBA), polyurethane, polyimide, polyolefin, nylon, or any combination thereof. The coating may be applied by, for example, over-extrusion, dip-coating, melt fusion, or heat shrinking. For example, PET shrink tube 202 has the advantage of providing an increased stiffness to a small diameter catheter shaft 201. On the other hand, a PEBA shrink tube 202 can be used with a larger diameter catheter shaft 201 where greater flexibility is desired. The type of sleeve 202 material may also be selected to complement other catheter components; for example, a nylon sleeve 202 may bond and interact better with a nylon expandable member such as a balloon or basket and/or a nylon wire guide lumen. Selection of coating materials, filar size and number, and diameter allow manipulation of the catheter shaft's 201 shore hardness to offer the desired functional properties.

Figure 3A:
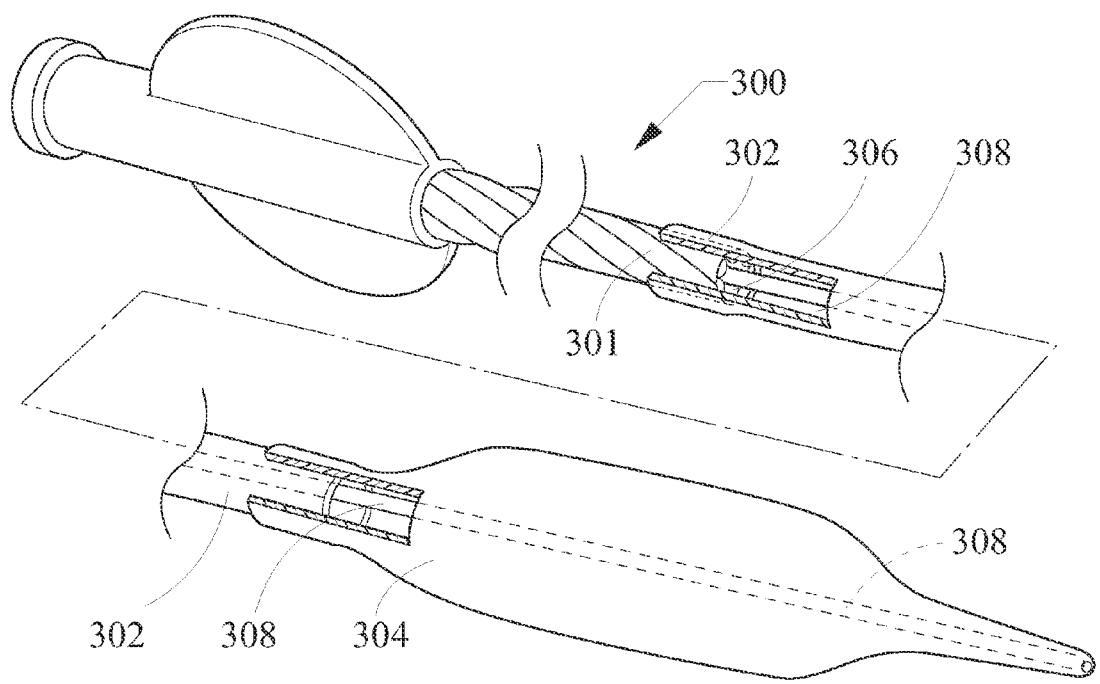
FIG. 3A is a perspective view of a catheter device having a distal extension and an inflation balloon, with an enlarged detail view of the features at the catheter's distal end.
Figure 3B:
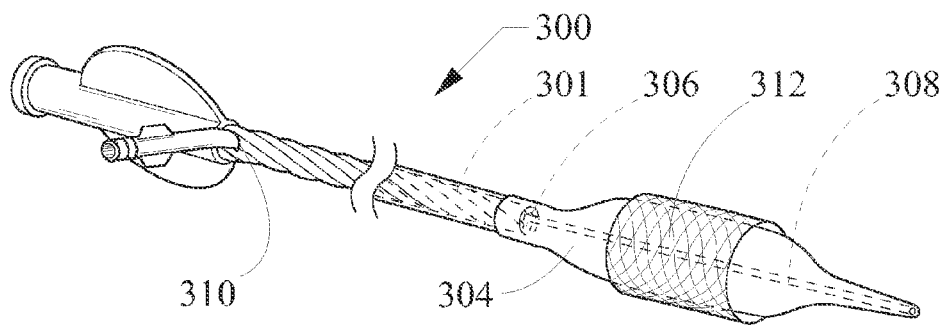
FIG. 3B is a perspective view of a catheter device with an inflation balloon.

FIGS. 3A-3B illustrate embodiments of balloon catheters 300 comprising a multifilar shaft 301. In the embodiment of FIG. 3A, the catheter shaft 301 has a distal extension 302, upon which is mounted an inflation balloon 304. The distal extension 302 can be formed of the same group of materials used in the coating (HDPE, PTFE, PEBA, PET, polyurethane, polyimide, polyolefin, nylon, or any combination thereof) and provides a shaft portion that may be more flexible than the shaft 301. As can clearly be seen in the detail illustration portion of FIG. 3A, the extension 302 encloses an inflation lumen 306 which continues from an inflation lumen 306 of the multifilar catheter shaft 301. The extension 302 also encloses a wire guide lumen 308. In the illustrated long wire configuration catheter 300, the wire guide lumen extends from the proximal end of the multifilar catheter shaft 301 and extends through the inflation balloon 304 at the distal end.

The embodiment illustrated in FIG. 3B has an inflation balloon 304 disposed directly on the distal end of the catheter shaft 301. An inflation lumen 306 of the multifilar catheter shaft 301 opens into the inflation balloon 304. A wire guide lumen 308 traverses the interior of the balloon 304, continuing the wire guide lumen 308 of the catheter shaft 301 to a point distal of the inflation balloon 304. As illustrated an expandable stent 312 may be positioned about the balloon 304. In an alternative embodiment, an expandable member other than a balloon (e.g., a basket) may be disposed near the distal end of the catheter shaft 301. Such an embodiment optionally may have a wire guide through the expandable member. At its proximal end the catheter 300 has a port 310 in fluid communication with the inflation lumen 306. In an alternative embodiment, the port 310 offers access to the guide wire lumen 308. The port 310 may be included in other embodiments, and in other positions on the catheter 300. In another alternative embodiment, the catheter shaft 301 has two ports 310, offering separate access to each of the inflation lumen 306 and the wire guide lumen 308. In other alternative embodiments, the port 310 may be useful for introducing another fluid such as a contrast fluid.

Figure 4A:
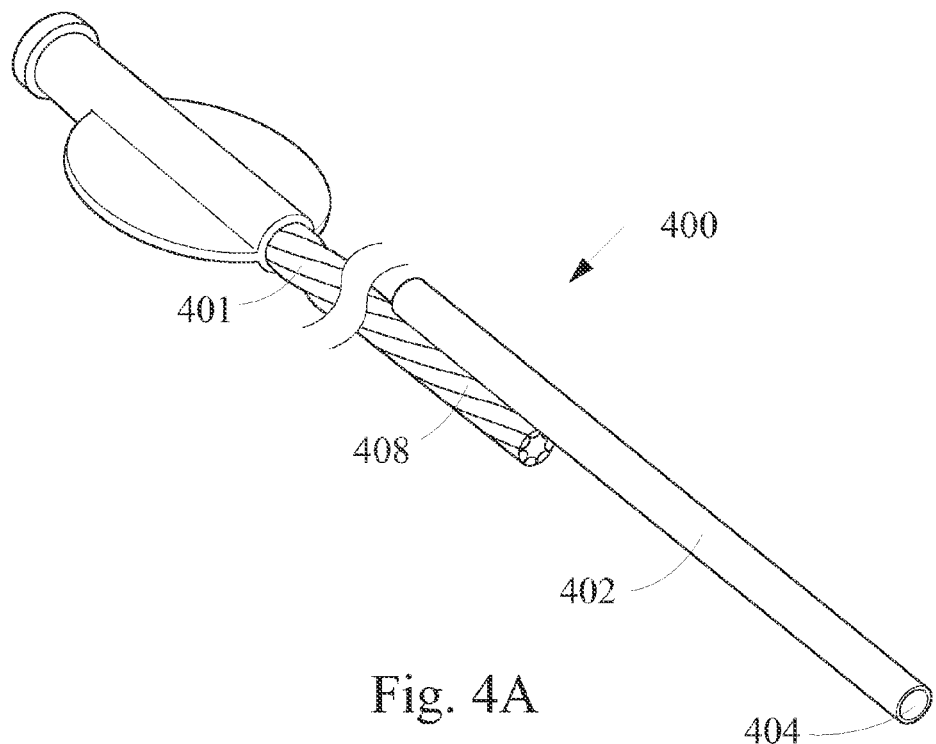
FIG. 4A is a perspective view of a catheter device having an external distal wire guide lumen structure, with an enlarged detail view of the features at the catheter's distal end.
Figure 4B:
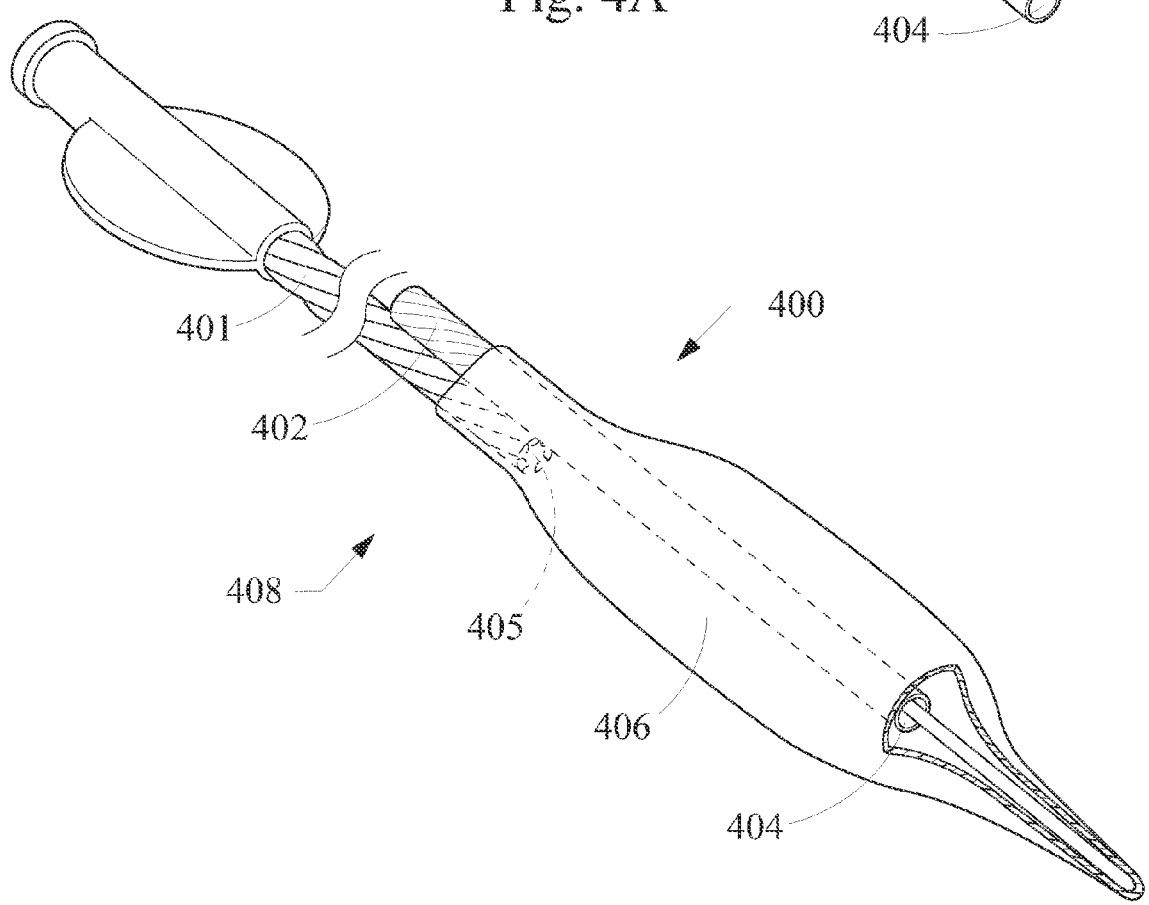
FIG. 4B is a perspective view of a catheter device having an external distal wire guide lumen structure and an inflation balloon, with an enlarged detail view of the features at the catheter's distal end.

FIGS. 4A-4B illustrate embodiments of a multifilar tube balloon catheter device 400 comprising a multifilar shaft 401 and further comprising an external, distally disposed short wire guide lumen structure in the form of a cannula 402 having a wire guide lumen 404 disposed therethrough. In FIG. 4A, the cannula 402 is attached on the distal end 408 of the multifilar catheter shaft 401 using an adhesive. Alternative means of attachment include, for example, forced convection heating, radio frequency heating, ultrasonic welding, and laser bonding. Alternatively, shrink tubing may be used as a manufacturing aid to help compress and fuse the cannula 402 to the multifilar catheter shaft 401. The shrink tubing may be removed and disposed of after the cannula 402 is connected to the catheter shaft 401, or may remain on as part of the connected structure. If the multifilar catheter shaft 401 has a coating, the cannula 402 may be bonded to the coating or directly to the catheter shaft 401. A heat shrink tubing, for example PEBA, may be applied over the entire assembly, which increases the strength of the assembly. In the embodiment shown in FIG. 4B, the cannula 402 is constructed of multifilar tubing. An inflation balloon 406 is mounted on the distal end 408 of the catheter shaft 401. An inflation lumen 405 of the catheter shaft 401 is open to the interior of the inflation balloon 406. The cannula 402 extends through the inflation balloon 406 and has an extension 407 on its distal end. A wire guide lumen 404 runs through the length of the cannula 402 and its extension 407. Although not shown, it should be appreciated that an expandable stent can be disposed about the balloon 406. The cannula 402 providing a wire guide lumen structure can be formed of HDPE, PTFE, PEBA, PET, polyurethane, polyimide, polyolefin, nylon, or any combination thereof. In one embodiment, the cannula 402 comprises a PTFE inner liner and a PEBA outer cover. Other materials may be used as an inner liner such as, for example, HDPE, PET, and polyimide.

Figure 4C:
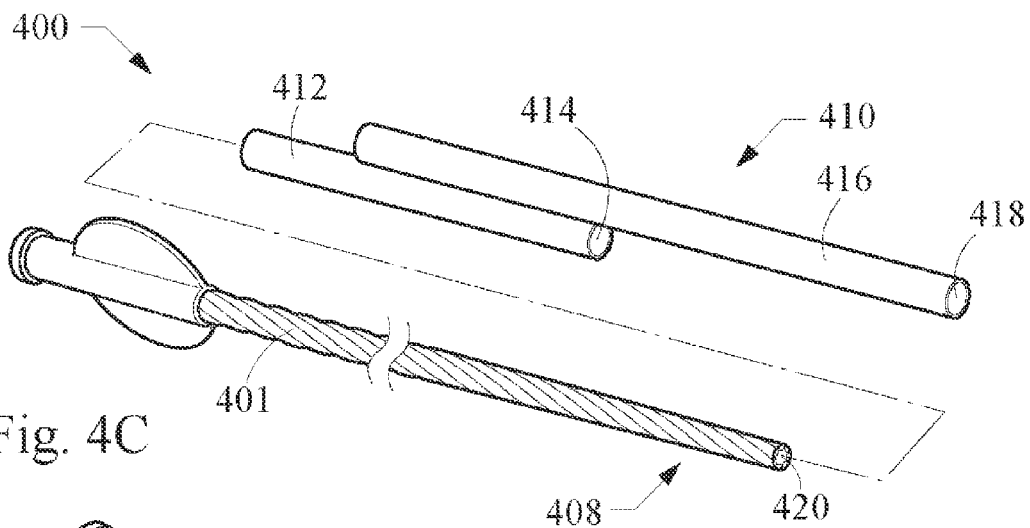
FIG. 4C is a perspective view of a catheter device with a distal dual lumen structure having a wire guide lumen structure and a mounting portion.

In FIG. 4C, a dual lumen structure 410 is disposed on the distal end 408 of the multifilar catheter shaft 401. A portion of the length of dual lumen structure 410 has a "figure 8" cross section. A mounting portion 412 of the dual lumen structure 410 has a lumen 414. The distal end 408 of the catheter shaft 401 fits into the lumen 414. The lumen 414 may be completely occupied by the distal end 408 of the catheter shaft 401, or may continue coaxially beyond the distal end 408 so as to form an extension. If the mounting portion 412 is placed as an extension, the lumen 414 is in fluid communication with a lumen 420 of the shaft 401. A wire guide portion 416 of the dual lumen structure 410 has a wire guide lumen 418 running therethrough. The dual lumen structure 410 is attached on the distal end 408 of the catheter shaft 401 using one of the attachment methods described for the embodiment shown in FIG. 4A. In this embodiment, the lumen 414 of the dual lumen structure is in fluid communication with a lumen 405 of the catheter shaft 401. In an alternative embodiment, a part of the mounting portion 412 is mounted inside the lumen 420 of the catheter shaft 401.

Figure 5A:
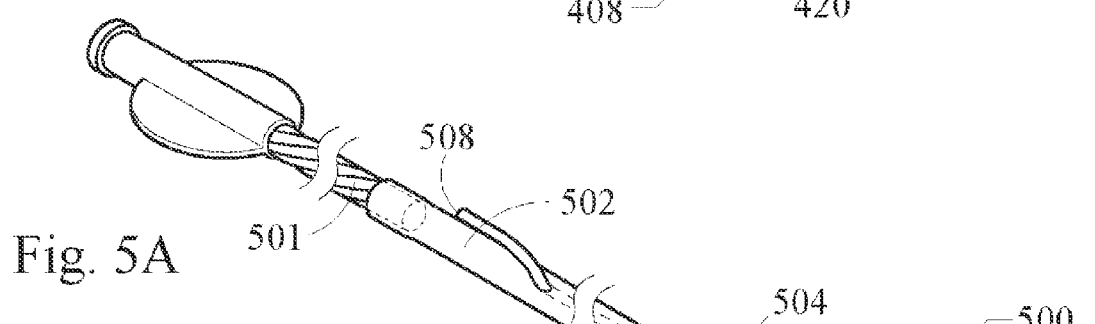
FIGS. 5A-5B show a side view of catheter devices having a distal extension and a wire guide lumen structure.
Figure 5B:
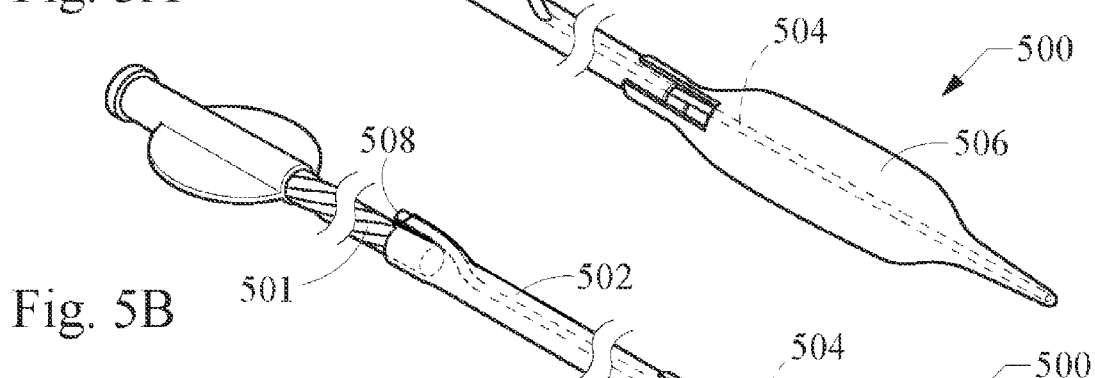
Figure 5C:
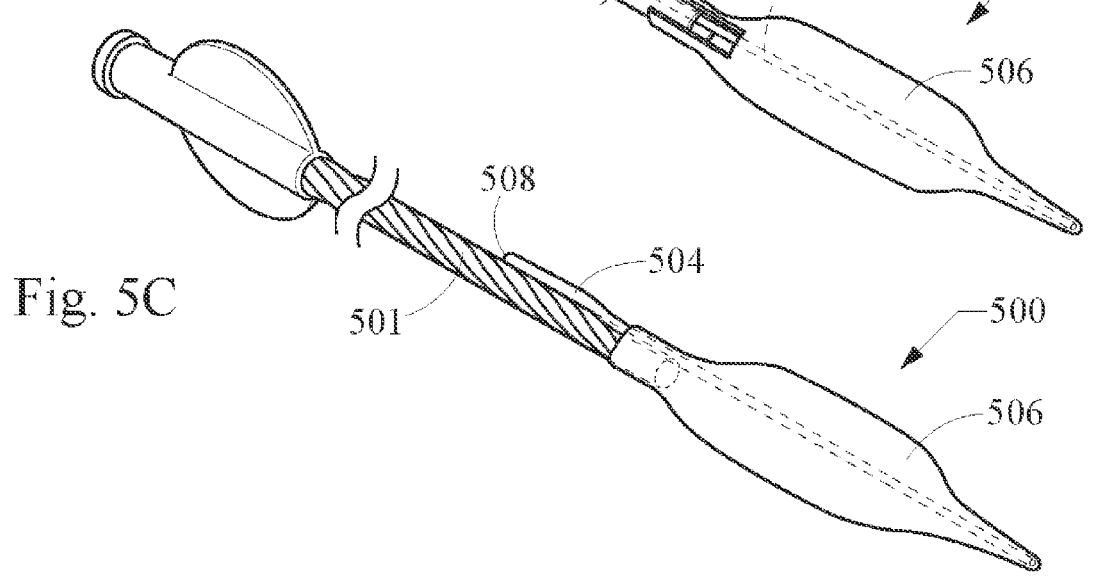
FIG. 5C is a side view of a catheter device having an external distal wire guide lumen structure and an inflation balloon.

FIGS. 5A-5C illustrate embodiments of a balloon catheter 500 incorporating a multifilar shaft 501 and having a short wire guide configuration. The embodiments shown in FIGS. 5A-5B each have a coaxial extension 502 of the multifilar shaft 501, a short wire guide lumen structure in the form of a tube 504, and an inflation balloon 506. The coaxial extension 502 may have the same or a different flexibility than the multifilar shaft 501. In the embodiment illustrated in FIG. 5A, the proximal end 508 of the tube 504 is disposed distal of the juncture of the extension 502 with the multifilar shaft 501. The tube 504 enters the extension 502 and extends through the distal end of the balloon 506. Thus, this embodiment comprises a distal extension of the shaft (in this case the coaxial extension 502) and the wire guide lumen structure 504, a portion of the wire guide lumen structure 504 being coaxial within the distal extension, another portion of the wire guide lumen structure 504 being outside the distal extension adjacent thereto.

In the embodiment illustrated in FIG. 5B, the proximal end 508 of the tube 504 is disposed proximal of the juncture of the extension 502 with the multifilar shaft 501. The tube 504 enters the extension 502 and proceeds through the distal end of the balloon 506. Thus, this embodiment comprises a distal extension of the shaft (in this case the coaxial extension 502) and the wire guide lumen structure 504, a portion of the wire guide lumen structure being coaxial within the distal extension, another portion of the wire guide lumen structure 504 being outside the shaft adjacent thereto. The embodiment illustrated in FIG. 5C does not have an extension. The balloon 506 is disposed on the distal end of the multifilar shaft 501. The proximal end 508 of the tube 504 is disposed proximal of the juncture of the extension 502 with the multifilar shaft 501 and is affixed to the exterior of the multifilar shaft 501. The tube 504 passes through the middle of the balloon 506 and proceeds through the distal end of the balloon 506. In each of the embodiments shown in FIGS. 5A-5C, the placement of the proximal end 508 of the tube 504 along the multifilar shaft 501 affects the flexibility of the shaft 501. Therefore, variation in the placement is useful in increasing or reducing flexibility as desired in other embodiments.

Figure 6:
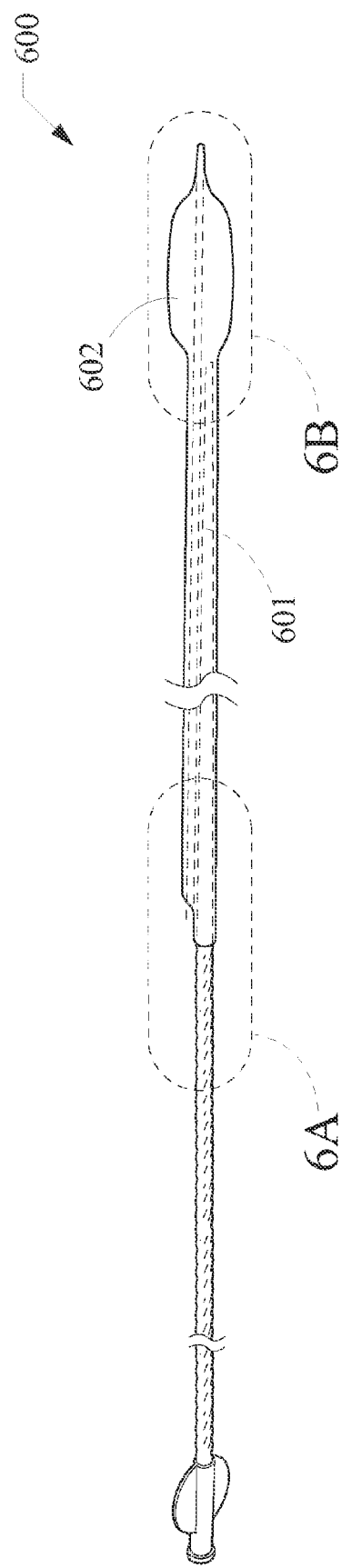
FIG. 6 is a side view of a tapered catheter device having an external distal wire guide lumen structure and an inflation balloon.
Figure 6A:
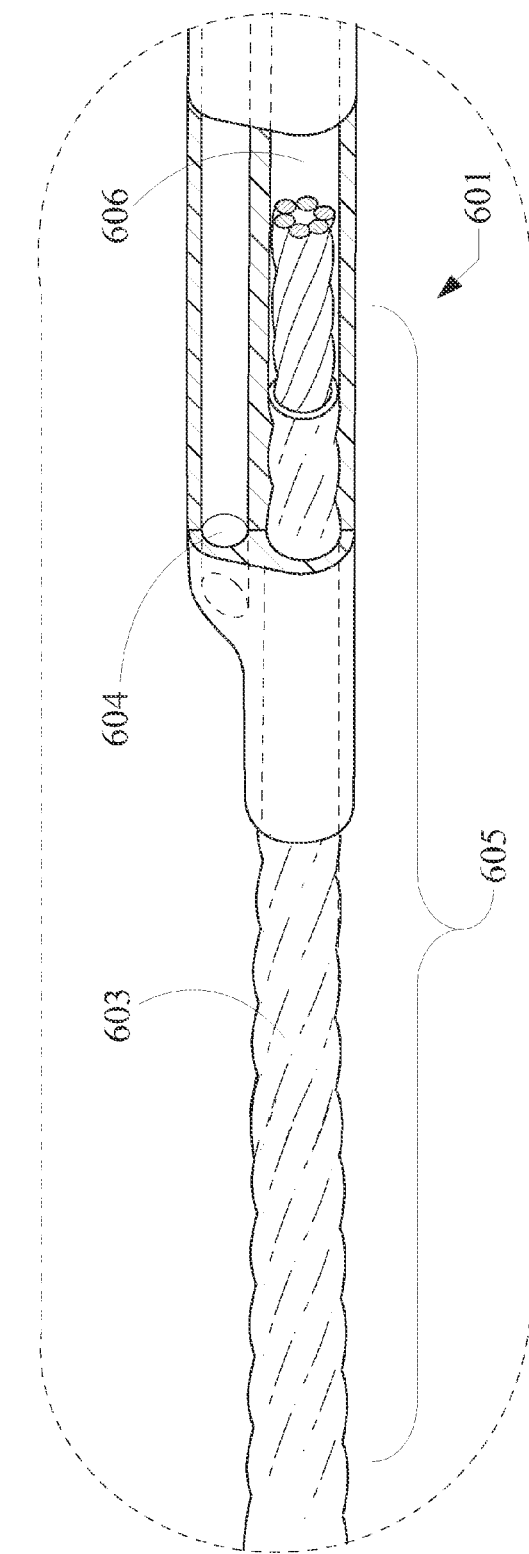
FIG. 6A is a detail of FIG. 6 and shows a longitudinal cross-sectional view of the tapering portion and external wire guide lumen of a catheter device.

FIG. 6 illustrates one embodiment of a balloon catheter 600 having an elongate shaft 601 comprising a multifilar tube. An inflation balloon 602 is disposed near the distal end. FIG. 6A is an enlarged detail illustration of a middle section of the catheter 600. As can be clearly seen in FIG. 6A, the shaft 601 includes an external wire guide lumen 604 and an internal inflation lumen 606. As shown in FIG. 6A, this embodiment the catheter shaft 601 is coated with a PEBA coating 603. The coating 603 serves to reduce friction during introduction of the catheter shaft 601 and provides a seal to prevent leakage of inflation fluid from the inflation lumen 606 through the walls of the shaft 601. As can also be seen in FIG. 6A, the catheter shaft 601 tapers distally to a smaller diameter along the region 605.

Figure 6B:
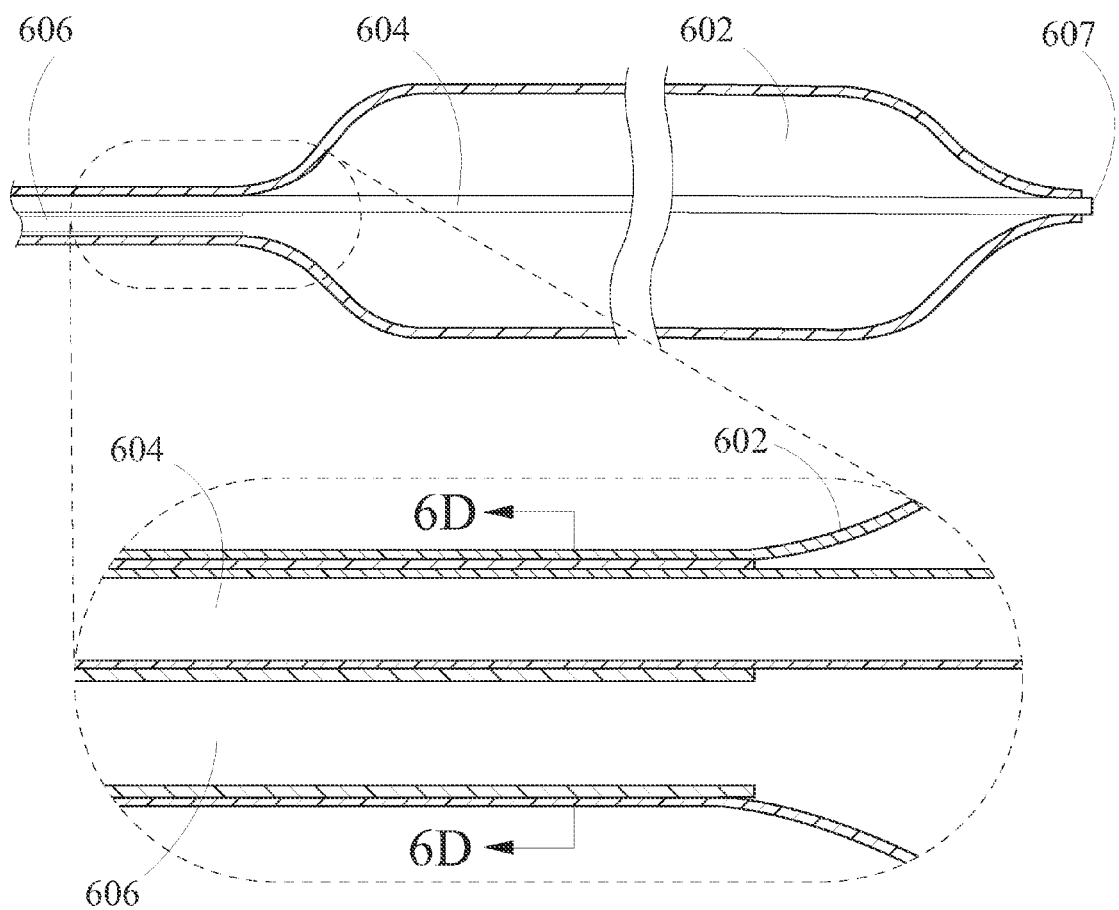
FIG. 6B is a detail of FIG. 6 and shows a longitudinal cross-sectional view of the distal portion of the catheter device, with an enlarged detail view of features where the catheter shaft meets the balloon.
Figures 6C, 6D:
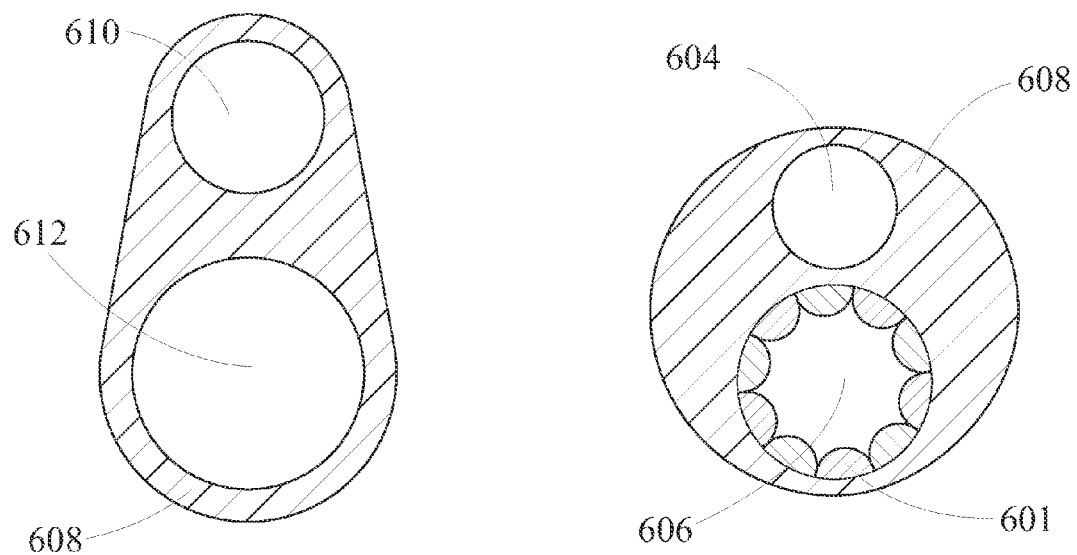
FIG. 6C is a transverse cross-sectional view of a dual-lumen mounting sleeve.
FIG. 6D is a transverse cross-sectional view along line 6D-6D of FIG. 6B showing two lumens of the catheter device surrounded by a mounting sleeve.

FIG. 6B is an enlarged detail illustration of a distal section of the balloon catheter 600. As shown in FIG. 6B, the inflation lumen 606 opens into the inflation balloon 602, and the wire guide lumen 604 extends through the balloon 602 to the distal end 607. FIG. 6B includes an enlarged detail portion more clearly illustrating the relationship between the balloon 602 and the two lumens (604 and 606). In this embodiment, the balloon 602 and wire guide lumen 604 are mounted to the shaft 601 with a PEBA shrink sleeve 608. As shown in FIG. 6C, a cross-sectional view of the sleeve 608 has approximately a figure-eight shape before mounting. The sleeve 608 has two central apertures (610 and 612) to allow mounting the sleeve 608 over the wire guide lumen 604 and the shaft. In this embodiment, after the balloon 602 and wire guide 604 are assembled to the shaft 601 together with the sleeve 608, the sleeve 608 is heated to shrink and form to the assembly of shaft 601, balloon 602, and wire guide 604. FIG. 6D is a transverse cross section along line 6D-6D of FIG. 6B, and shows the finished configuration. The sleeve 608 forms to the shaft 601 and leaves open the inflation lumen 606 and the wire guide lumen 604.

Cross-lumen communication may be prevented. For example, the walls of the multifilar tube of the elongate shaft 601 may be porous, and pressure exerted on an inflation fluid in the inflation lumen 606 may urge inflation fluid into the wire guide lumen 604. According to one aspect, this may be prevented by lining the wire guide lumen 604 with a liner such as, for example, PTFE, although other materials may be used. Furthermore, an inner coating segment may be placed over the elongate shaft 601 beneath the proximal breach or side opening of the wire guide lumen 604. The inner coating segment may be, for example, PEBA. The inner coating segment may be implemented to alter flexibility in the area of the segment, for example to avoid abrupt changes in flexibility. In one embodiment, the proximal end of the segment terminates at about halfway through the taper and the distal end of the segment terminates just distal of the proximal breach or side opening of the wire guide lumen 604. According to another aspect, cross-lumen communication may be prevented by placing the coating 603 over essentially the entire length of the elongate shaft 601, and the sleeve 608 may subsequently be placed over the coating 603 and elongate shaft 601. According to yet another aspect, cross-lumen communication may be prevented by simply making the walls of the sleeve 608 thicker. A 0.001 inch (0.025 mm) wall thickness of the coating 603 or sleeve 608, for example, may be sufficient. As mentioned previously, the coating 603 and sleeve 608 may be PEBA or another suitable material. These principles may be implemented in other embodiments of the invention as may be desirable due to fluid being passed through or injected into one of the lumens.

Figure 7A:
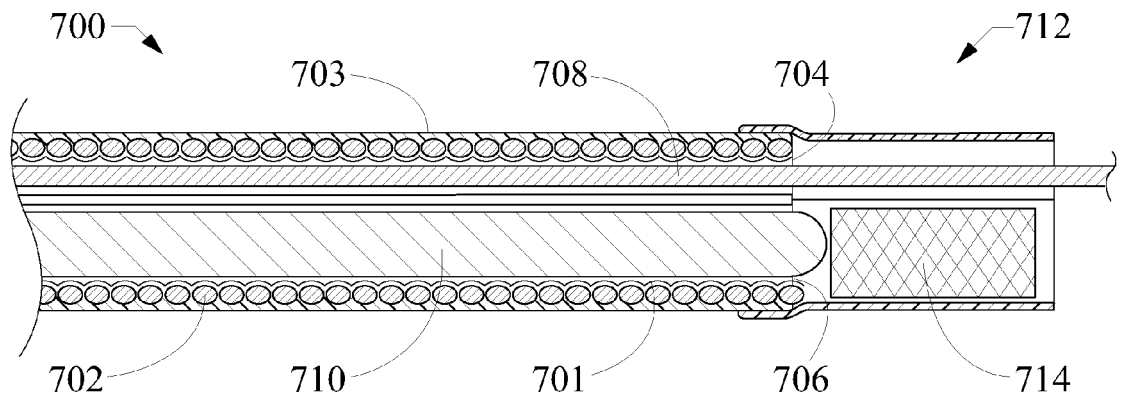
FIGS. 7A and 7B illustrate a cross-sectional view of another embodiment of a catheter device.
Figure 7B:
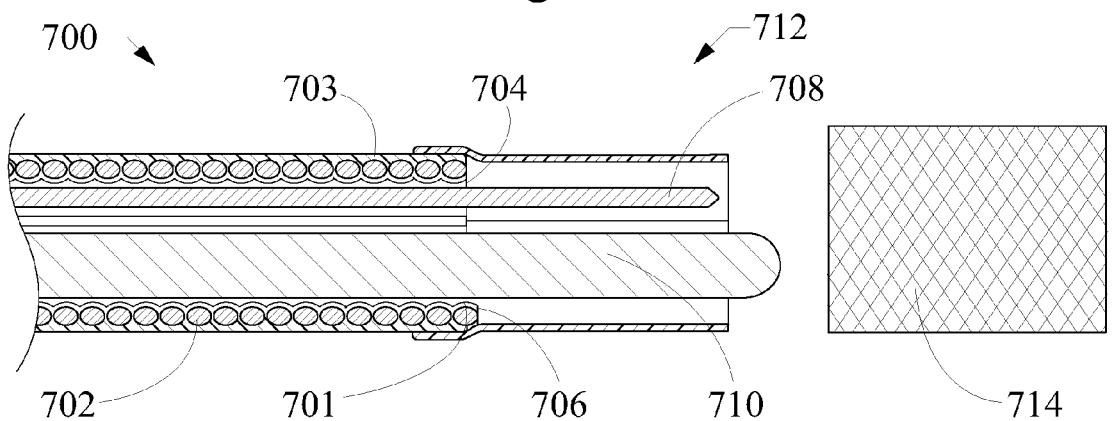

FIGS. 7A-7B illustrate a cross-sectional view of a portion of a catheter device 700 according to one aspect of the present invention. A shaft wall comprising multiple filars 702 includes an inner coating 701 and an outer coating 703, and surrounds a first lumen 704 and a second lumen 706. A wire guide 708 extends through the first lumen 702, and a stent-deployment shaft 710 extends through the second lumen 706. As shown in FIG. 7A, the catheter device 700 includes a distal extension 712 that houses a self-expandable stent 714. FIG. 7B illustrates the stent 714 having been pushed out of the second lumen 706 by the stent-deployment shaft 710 such that the stent 714 is deployed. Prior to deployment of the stent 714, the wire guide 708 is typically retracted into the shaft wall or lumen 704 so as not to interfere with deployment of the stent 714.

Figure 8:
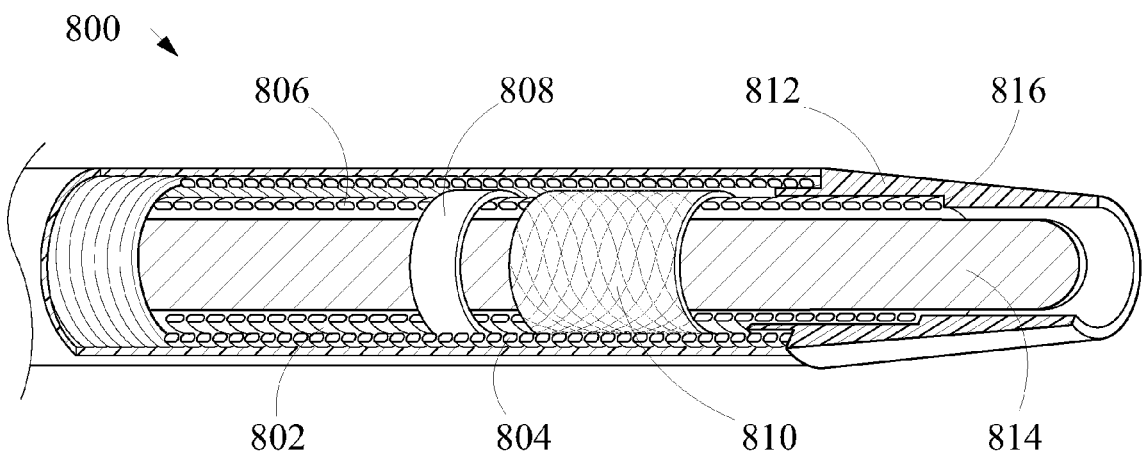
FIG. 8 illustrates a partial cross-sectional view of yet another embodiment of a catheter device.

FIG. 8 illustrates a partial cross-sectional view of another embodiment of a catheter device 800, including a self-expanding stent 810. The catheter device 800 has a central lumen 802 surrounded by a first, outer tubular multifilar body 804. A second, inner multifilar cable tube is coaxially disposed in the central lumen 802 for use as a pusher 806. The pusher 806 has a protruding engagement surface 808 for pushing the self-expanding stent 810 out of the central lumen 802 or for holding the stent 810 as the outer tubular multifilar body 804 is being pulled in a proximal direction. A tapered tip 12 is mounted on the distal end of the pusher 806, and provides a minimally traumatic leading surface for the catheter device 800. A wire guide 814 extends through a central wire guide lumen 816 of the pusher 806. Optionally, apertures (not shown) may be provided through the side of the outer tubular body 804 and the pusher 806 to permit the wire guide 814 to exit the central lumen 802 and the wire guide lumen 816 at an intermediate location. The self-expanding stent 810 is adapted to be deployed when a user retracts the outer tubular body 804 proximally while holding the pusher 806 substantially in place. The protruding engagement surface 808 of the pusher 806 holds the self-expanding stent 810 substantially in place while the outer tubular body 804 is withdrawn from around it. Once the stent 810 is deployed, the pusher 806 and wire guide 814 are withdrawn, leaving the stent 810 in the position where it was deployed.

Figure 9B:
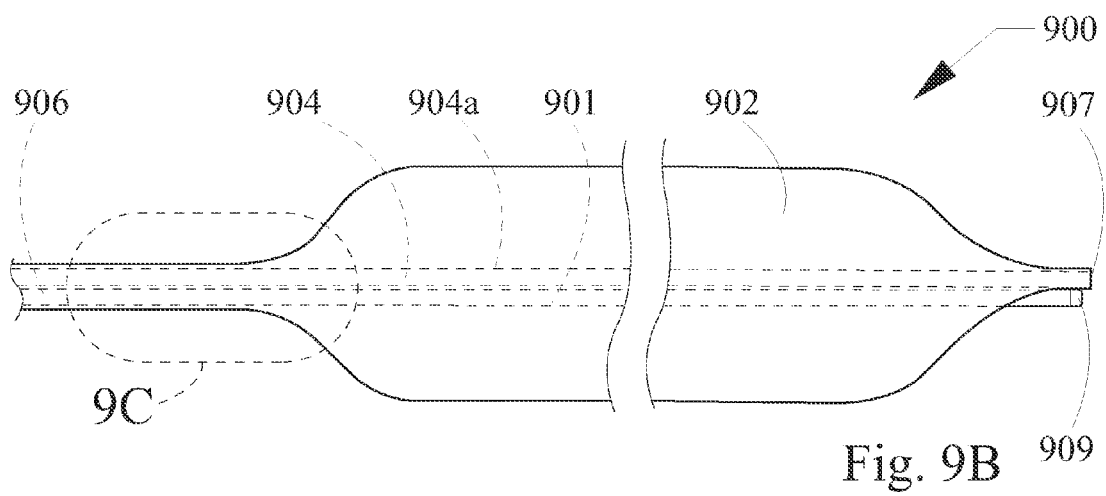
FIGS. 9-9E depict still another catheter device embodiment, including a wire guide lumen tube.
Figure 9C:
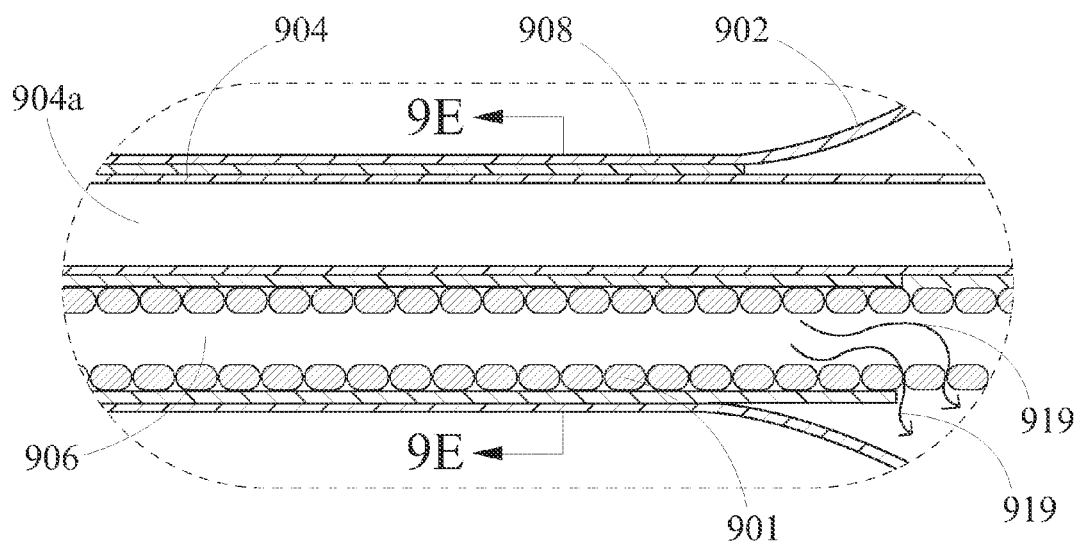
Figure 9D:
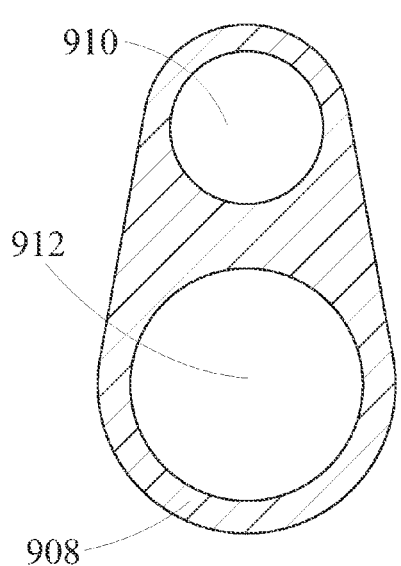
Figure 9E:
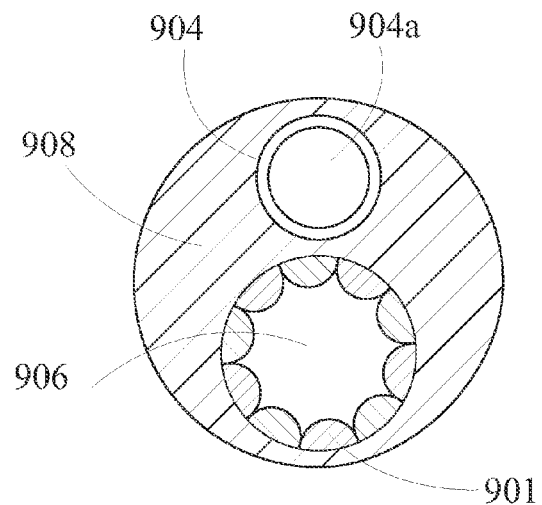

FIGS. 9-9E illustrate one embodiment of a balloon catheter device 900 having an elongate multifilar tube shaft 901 and being configured for use in a short-wire application using a wire guide. An inflation balloon 902 is disposed near the distal end of the device 900 and is sealed thereto. FIG. 9A is an enlarged detail illustration of an intermediate section of the catheter 900. As shown in FIGS. 9 and 9A, the catheter 900 includes an internal shaft lumen 906 and an external wire guide lumen 904a that is housed by a wire guide tube 904. As shown in FIG. 9A, the shaft 901 may be coated with a PEBA or other coating 903. In one aspect, the coating 903 may help to reduce friction during introduction of the catheter shaft 901 and provide a seal that prevents leakage of inflation fluid from the shaft lumen 906 through the multifilar wall of the shaft 901. Those of skill in the art will appreciate that a coating 903 may be disposed on the exterior of the shaft 901, or it may be disposed as a lining/coating on the interior/lumenal surface of the shaft lumen 906, or both. As is also depicted in FIG. 9A, the catheter shaft 901 tapers distally to a smaller diameter along a narrowing transitional region 905, which provides for a distal shaft portion that is more flexible than the proximal shaft portion. An increased distal flexibility may allow the catheter device 900 to be more readily navigated through tortuous passages.

FIG. 9B is an enlarged detail illustration of a distal section of the balloon catheter 900. As shown in FIG. 9B, both the shaft 901 and the wire guide lumen tube 904 extend through the balloon 902 to the distal end 907. The distal end of the shaft 901 may be provided with a sealing tip 909, which preferably has an atraumatic distal profile. FIG. 9C shows an enlarged detail portion of FIG. 9B to illustrate the relationship between the balloon 902 and the wire guide and shaft lumens (904a and 906). The portion of the shaft 901 inside the balloon 902 does not include the coating 903, and the filars forming the wall of the shaft 901 do not form a fluid-tight barrier. As a result, and as indicated by arrows 919, the shaft lumen 906 may be used effectively as an inflation lumen because inflation fluid introduced therethrough can pass through an intralumenal portion the multifilar wall of the shaft 901 (inside the lumen of the balloon 902) to inflate the balloon 902. However, the wire guide lumen tube 904 most preferably is configured not to allow fluid communication from the shaft lumen 906 or the lumen of the balloon 902. Specifically, the wire guide lumen tube 904 is configured such that inflation fluid passing through the wall of the shaft 901 into the lumen of the balloon 902 will not escape through the wire guide lumen 904a. As is also shown in this embodiment, the shaft 901 extending through the length of the balloon 902 may provide longitudinal support for the balloon 902.

As is also shown in this embodiment, the balloon 902 and wire guide lumen tube 904 may be mounted to the shaft 901 with a shrink sleeve 908. As shown in FIG. 9D, the sleeve 908 has approximately a figure-eight shape before mounting. The sleeve 908 includes two central apertures (910 and 912) to allow for mounting the sleeve 908 over the wire guide lumen tube 904 and the shaft 901. In this embodiment, after the balloon 902 and wire guide tube 904 are assembled to the shaft 901 together with the sleeve 908, the sleeve 908 may be heated to shrink and form to the assembly of the shaft 901, balloon 902, and wire guide tube 904. FIG. 9E is a transverse cross section view along line 9E-9E of FIG. 9C that shows the finished configuration. The sleeve 908 forms to the exterior surface of the shaft 901 and leaves open the shaft lumen 906 and the wire guide lumen 904a. As is shown in FIG. 9A, the sleeve 908 may extend over and proximally beyond the wire guide tube 904. Accordingly, a wire guide aperture 914 may be skived out or otherwise created to provide access to the wire guide lumen 904a. Those of skill in the art will appreciate that, in lieu of using a sleeve, the coating 903 may be extended to contact the wire guide tube 904 and/or the balloon 902 to provide a seal of the coating 903 with the wire guide tube 904 and/or the balloon 902, or that other means for securing the wire guide tube 904 and balloon 902 to the shaft 901 may be used within the scope of the present invention.

Figure 10:
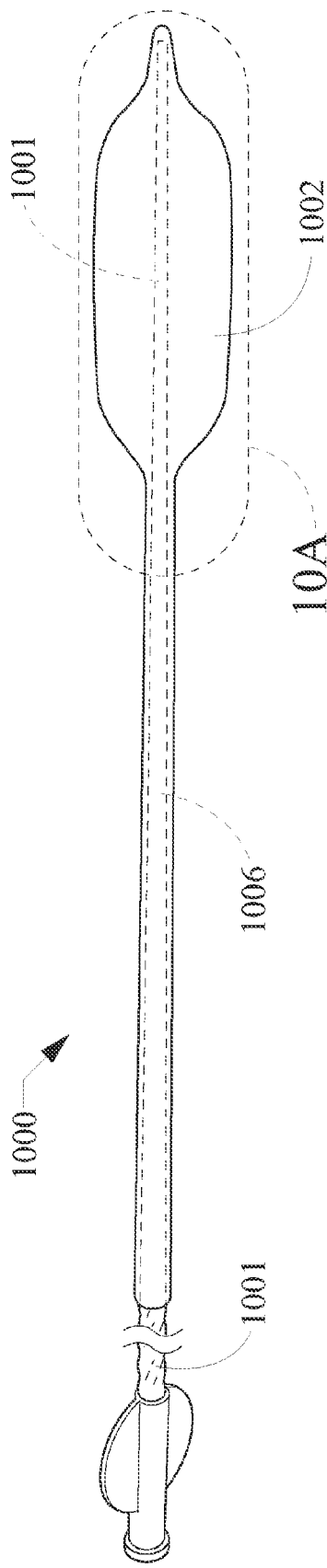
FIGS. 10-10A show yet another catheter device embodiment.
Figure 10A:
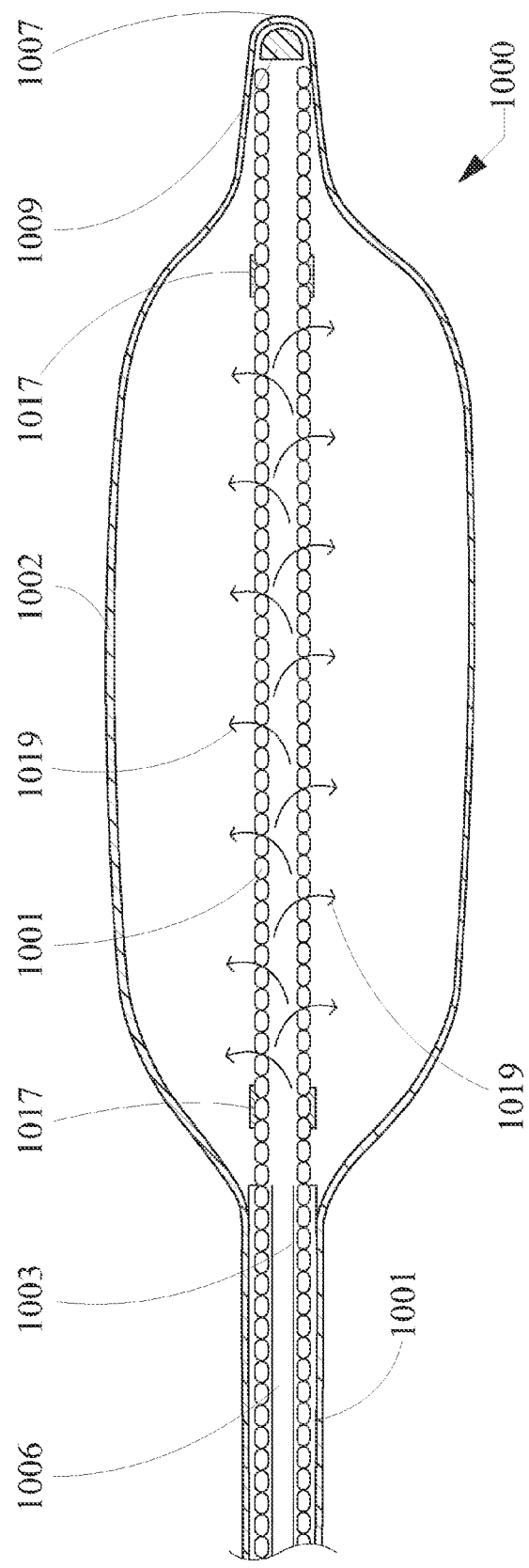

FIGS. 10-10A illustrate an embodiment of a balloon catheter device 1000 having an elongate multifilar tube shaft 1001 and being configured for use without a wire guide. In one aspect, the embodiment of FIG. 10 may be configured such that it may be manipulated during navigation in the same manner as a wire guide. An inflation balloon 1002 is disposed near the distal end of the device 1000 and is sealed thereto in a manner that forms a continuously sealed length of the shaft lumen 1006 proximal of the balloon 1002 in cooperation with an internal shaft lumen coating 1003. In one aspect, the coating 1003 may help to provide a seal that prevents leakage of inflation fluid from the shaft lumen 1006 through the multifilar wall of the shaft 1001. The catheter shaft 1001 may include a tapering diameter that is smaller distally than proximally and provides for a distal shaft portion that is more flexible than the proximal shaft portion while maintaining desirable pushability and trackability.

FIG. 10A is an enlarged detail illustration of a distal section of the balloon catheter 1000. As shown in FIG. 10A, the shaft 1001 extends through the balloon 1002 to the distal end 1007. The distal end of the shaft 1001 may be provided with a sealing tip 1009, which preferably has an atraumatic distal profile. The coating 1003 substantially covers the surface of the shaft lumen 1006 through the proximal length of the shaft 1001 and terminates near the proximal end of the balloon 1002 such that an intralumenal portion of the shaft 1001 (inside the interior space of the balloon, at least part of which forms a lumen of the balloon 1002) does not include the coating 1003, and the filars forming at least that portion of the wall of the shaft 1001 do not form a fluid-tight barrier. As a result, and as indicated by arrows 1019, the shaft lumen 1006 may be used effectively as an inflation lumen because inflation fluid introduced therethrough can pass through the multifilar wall of the shaft 1001 to inflate the balloon 1002. Those of skill in the art will appreciate that a coating may be used on the shaft exterior in addition to or instead of the lumenal shaft coating 1003, and that, if a coatings are present on both the interior and exterior shaft surfaces, each coating may include the same or different materials as the other coating. In this embodiment, the shaft 1001 also provides longitudinal support for the balloon 1002. The shaft portion disposed within the balloon 1002 may include a pair of radio-opaque markers 1017 configured to allow a user to fluoroscopically visualize the position of the balloon 1002. Suitable radio-opaque markers may include swaged metal (such as, for example, stainless steel, platinum, gold) or an polymer infused with barium or another radio-opaque material.

In one preferred embodiment, a balloon catheter device such as the balloon catheter 1000 lacking an external wire guide structure may be constructed such that it may function similar to a wire guide. Specifically, the catheter 1000 may be configured such that it has a small outer diameter, is sufficiently flexible to pass through a tight curvature or tortuous passageway, and has pushability and trackability sufficient to be navigated through such tightly curved and/or tortuous pathways in the same manner as a wire guide, thereby obviating the need for a separate wire guide. Those of skill in the art will appreciate that a preferred outer diameter will be different for different applications, but the outer diameter a catheter embodiment configured for use in peripheral blood vessels may be in the range of about 0.040-0.055 inches, and that the outer diameter may differ along the length of the catheter embodiment.

In some embodiments, the shaft coating (if any) may be a material other than PEBA, and may include the same material or different material than the material in a mounting sleeve used to mount a balloon (for example, HDPE, PTFE, PET, polyurethane, polyimide, polyolefin, nylon, or any combination thereof). The balloon catheters of the present invention may be adaptable for use with expandable stents as is illustrated, for example, in FIG. 3B. In the embodiments described above, a flexible stylet (not shown) may be inserted through the inflation lumen for use during advancement/navigation of the catheter device to a desired location. Such a stylet may be used to increase stiffness and pushability in a circumstance where that is desirable (such as, for example, if the catheter is being used to cannulate a lesion). Use of a stylet that is shaped (such as, for example, with a curve of up to about 70°) may also allow a user to reshape the distal end of the catheter shaft in a manner that may, for example, allow easier indication and navigation of branch vessels. A preferred stylet will not extend beyond the distal end of the catheter device.

Figure 11:
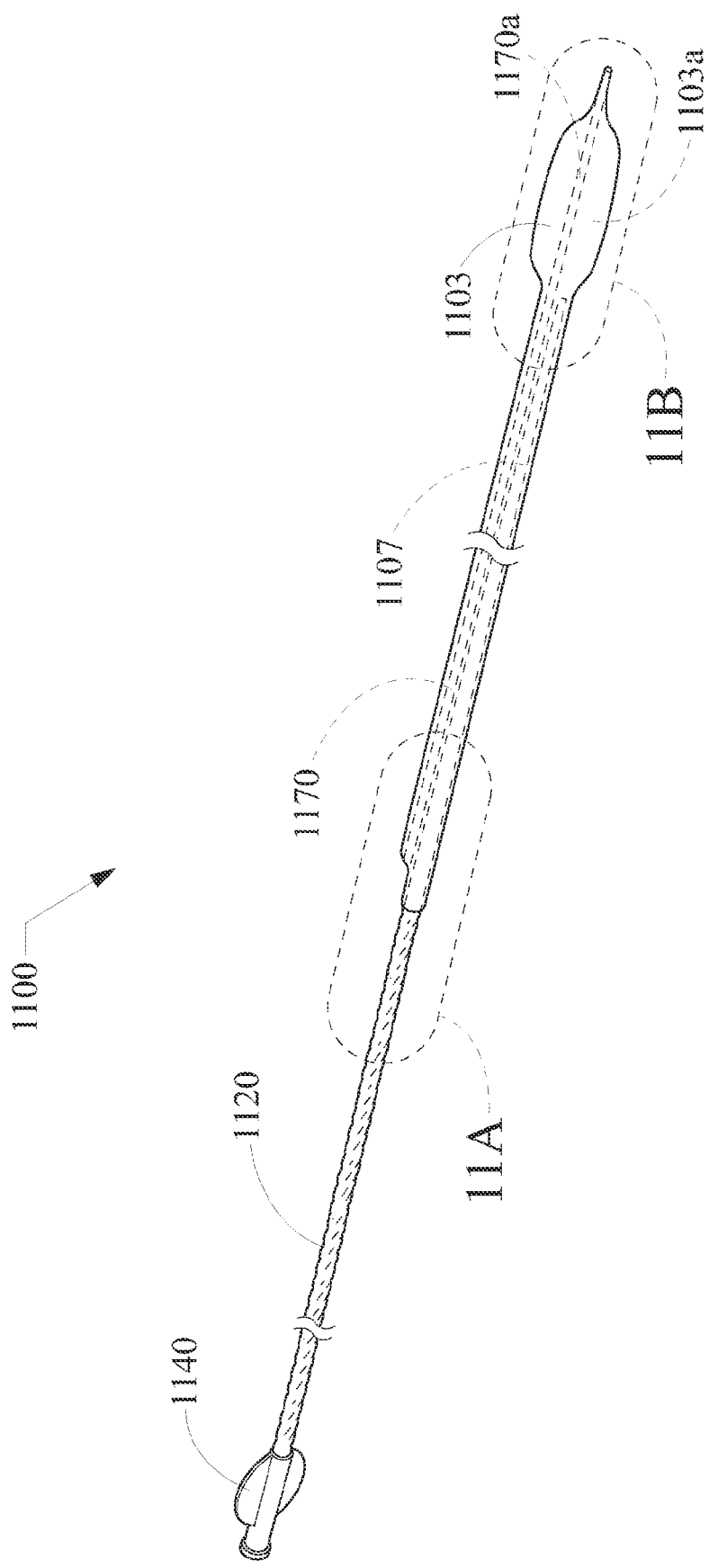
FIG. 11 is a side view of a multifilar catheter device having a distal wire guide lumen structure and an inflation balloon.
Figure 11B:
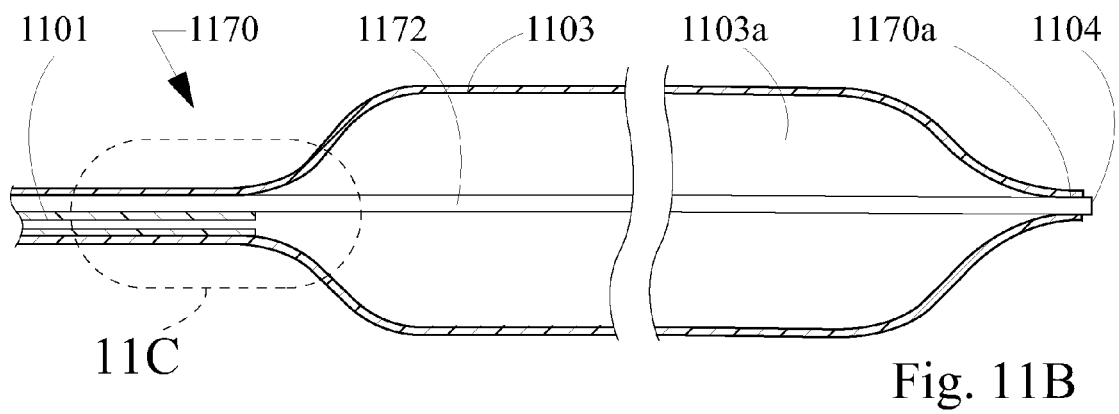
Figure 11C:
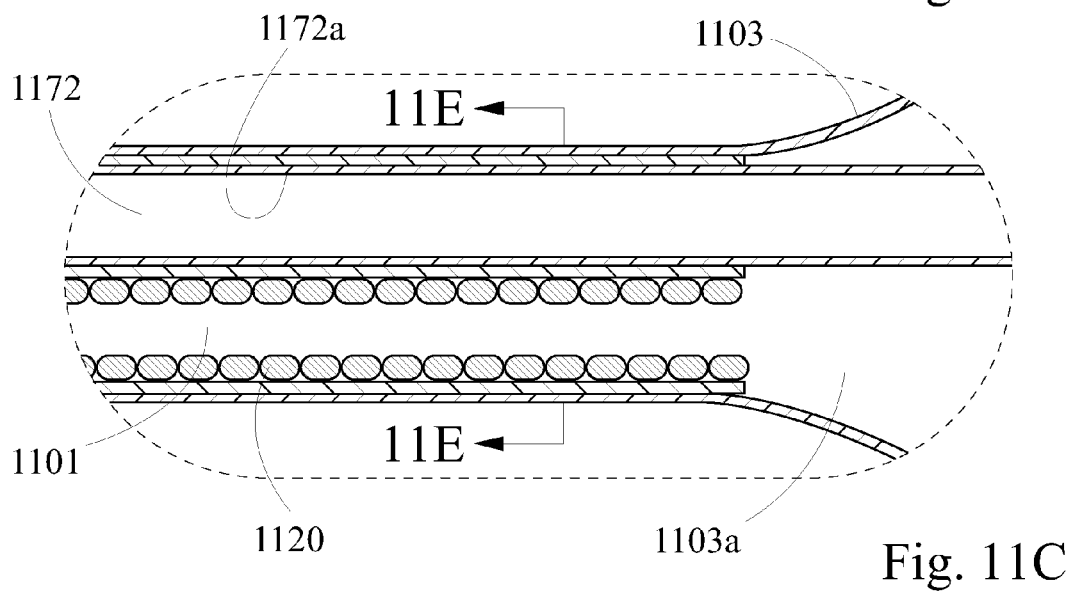
FIG. 11C is a transverse cross-sectional view of a dual-lumen mounting sleeve.
Figures 11D, 11E:
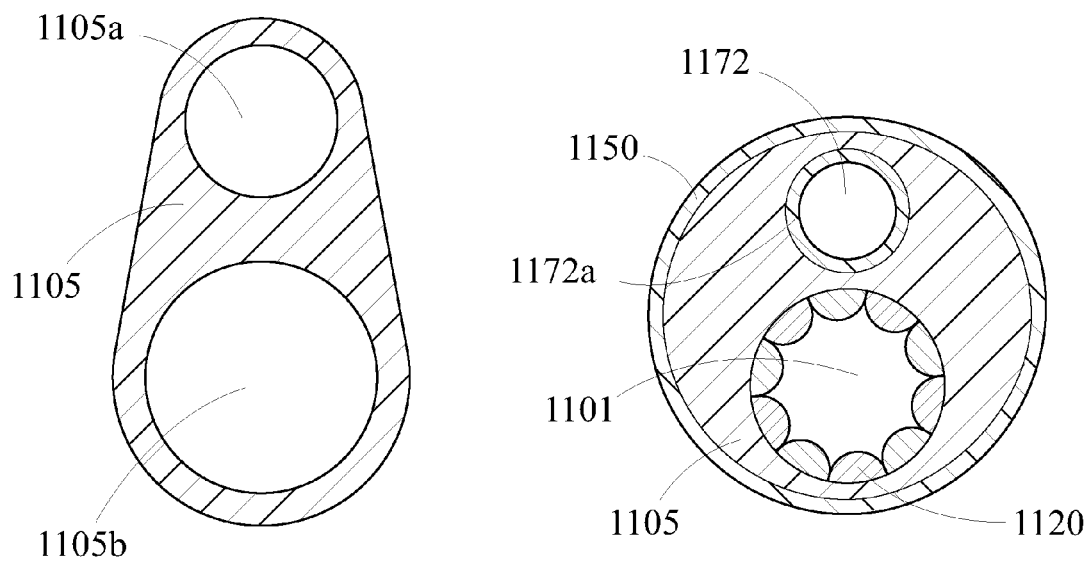
FIGS. 11D-11G show transverse cross-sectional views of the catheter device of FIG. 11.
Figure 11F:
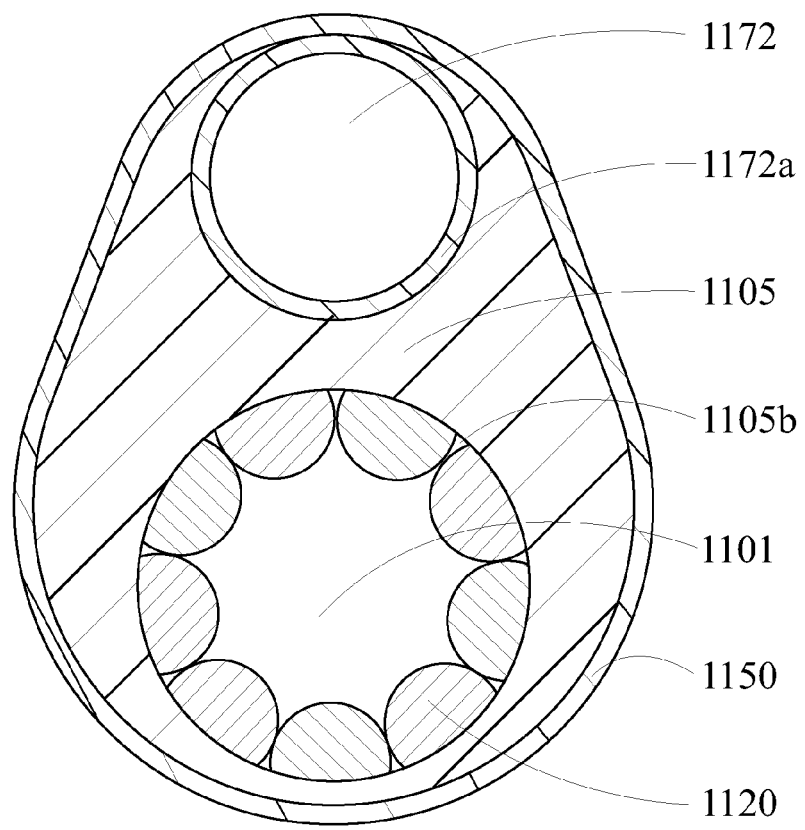
Figure 11G:
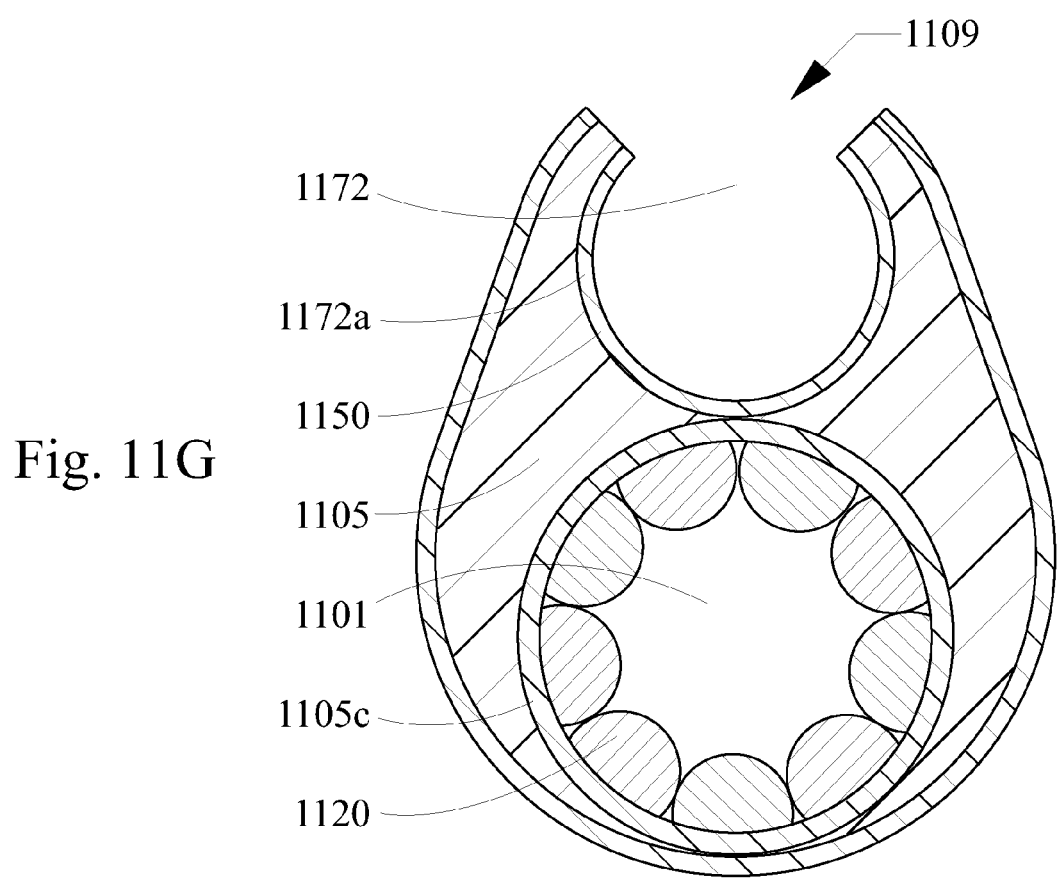

Another balloon catheter device embodiment 1100 is shown with reference to FIGS. 11-11G. The catheter device 1100 includes an elongate shaft 1107 including a monolayer multifilar tube 1120. An inflation balloon 1103 is disposed near the distal end of the device. A hub 1140 is disposed adjacent the proximal end of the device. FIG. 11A is an enlarged detail illustration of a distal-middle portion of the device 1100, showing a magnified longitudinal section view that includes a proximal portion of a wire guide lumen structure 1170 configured for use of the device in a short wire guide configuration. The wire guide lumen structure 1170 includes a wire guide lumen 1172 that extends substantially parallel with an inflation lumen 1101 of the shaft 1107.

In the illustrated embodiment, substantially the entire length of the shaft 1107 may include an outer layer 1150 as a coating. A preferred coating is a thermoplastic polymer such as, for example, a polyester or polyether block amide (e.g., PEBAX®). A preferred coating will provide a desirable lubricity profile that exhibits low friction during introduction of the device through, for example, a blood vessel. A preferred coating will also provide a fluid-tight seal configured to prevent leakage of pressurized inflation fluid (for example, at pressures in a normal operating range up to about 8-14 atm, and preferably configured to prevent leakage at pressures exceeding normal ranges, for example, up to or exceeding about 27 atm).

A preferred catheter shaft 1107 tapers from a greater proximal outer diameter (such as, for example, about 0.048 to about 0.052 inches) to a lesser distal diameter (such as, for example, about 0.044 to about 0.040 inches). Those of skill in the art will appreciate that the lesser distal diameter may present improved trackability for navigation of tortuous passages.

As is shown in FIGS. 11B and 11C (which is an enlarged detail view of FIG. 11B), the inflation lumen 1101 of the catheter device 1100 is open to and provides fluid communication with the balloon lumen 1103a of the balloon 1103. A distal portion 1170a of the wire guide lumen structure 1170 including the wire guide lumen 1172 also extends through the balloon lumen 1103a and through the distal end of the balloon 1103 to a distal tip 1104. The distal end portion 1170a of the wire guide lumen structure 1170 preferably is very flexible (high trackability), and it may provide an advantage in directing the device 1100 along a wire guide (not shown) through particularly tortuous passages. FIG. 11B also shows the attachment of the balloon 1103 to the device 1100. Those of skill in the art will appreciate that, in another embodiment within the scope of the present invention, the balloon 1103 may be attached to the tube 1120 and configured such that the distal wire guide lumen structure portion 1170a extends exterior (of the balloon lumen 1103a) and adjacent the balloon 1103.

FIG. 11D shows a transverse cross-section of a dual-lumen thermoset sleeve 1105, which has a generally figure-8 cross-section and includes an upper lumen 1105a and a lower lumen 1105b. The sleeve 1105 preferably is constructed of a thermoplastic binder material such as, for example, a polyolefin, polyester or polyether block amide (PEBA), or other appropriate polymeric material having thermoplastic materials suitable for helping to form the wire guide lumen structure 1170 and to attach it to the tube 1120. As depicted in FIGS. 11E-11F (each of which represents a transverse cross-sectional view along line 11E-11E of FIG. 11A), the upper lumen 1105a of the sleeve 1105 defines the wire guide lumen 1172. The wire guide lumen 1172 may include a wire guide lumen liner 1172a, which preferably is made of a lubricious polymer that can form a thin wall with high strength such as, for example, PTFE, polyethylene, polyimide, or a similar material. In one aspect, the liner 1172a may help prevent fluid from leaking from the inflation lumen 1101 through pores of the tube 1120 into the wire guide lumen 1172. Preventing inflation fluid from leaking out of the inflation lumen is preferable for at least the reason that a substantially patent fluid lumen is required to allow passage of inflation fluid at a pressure and rate desired for proper inflation and deflation of the balloon. In another aspect, the portion of the sleeve 1105 between the sleeve lumens 1105a and 1105b may be provided with a desired thickness such as, for example, about 0.001 inches to minimize the likelihood of cross-lumen communication between the inflation lumen 1101 and wire guide lumen 1172.

The lower lumen 1105b surrounds the tube 1120. The outer layer coating 1150 of the device may extend over and surround the exterior of the sleeve 1105. As shown in FIGS. 11E-11F, the thermoset sleeve 1105 has been heated to conform around the wire guide lumen 1172 and tube 1120. FIG. 11E shows the sleeve 1105 as having been formed with a round cross-section, and FIG. 11F shows the sleeve 1105 as having been formed with an out-of-round cross-section. The latter configuration is preferred when the device 1100 is to be used in conjunction with a guide sleeve (not shown) through which contrast fluid may be injected, because the out-of-round profile will more readily permit contrast fluid to flow through a circular-cross-section guide sheath lumen and around the sleeve 1105. However, it is preferable that the cross-sectional height not be greatly different than the cross-sectional width.

A wire guide aperture 1109 is described with reference to FIGS. 11A and 11G (which is a transverse cross-sectional view of FIG. 11A along line 11G-11G). In order to facilitate use of the catheter device 1100 in a short wire configuration, a wire guide aperture 1109 is provided near the proximal end of the wire guide lumen structure 1170. The wire guide aperture 1109 may be formed by skiving an opening through the outer layer 1150, upper surface of sleeve 1105, and (if present) wire guide lumen liner 1172a. This aperture 1109 will, for example, allow a wire guide (not shown) directed from the distal end 1104 through the wire guide lumen 1172 to exit. As described above, mounting the device 1100 onto a wire guide in this manner may facilitate rapid introduction and/or exchange of the device 1100 along the wire guide. In order to provide additional protection against cross-lumen leakage in the aperture region, an additional barrier 1105c may be provided around the circumference of the shaft 1107 along a shaft region adjacent the aperture 1109. The barrier 1105c preferably will be formed of a high-strength polymer that preferably is impermeable to inflation fluid such as, for example, a polyether block amide or similar material.

EXAMPLE 1

Figure 12A:
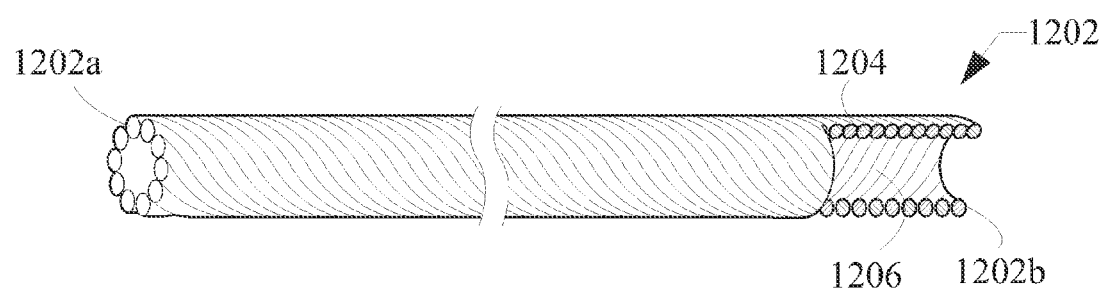

An exemplary method of making a wire-guided balloon catheter 1200 is described with reference to FIGS. 12A-12K. Those of skill will appreciate that this and other embodiments may be constructed using alternative methods within the scope of the present invention. As shown in FIG. 12A, a multifilar tubular shaft 1202 is provided, including a monolayer tubular shaft of ten filars coiled together to form a shaft wall 1204 defining a shaft lumen 1206. The shaft 1202 includes a proximal end 1202a and a distal end 1202b, and it has desirable pushability and trackability characteristics, with a structure that tapers from a proximal outer diameter of about 0.05 inches to a distal diameter of about 0.04 inches.

Figure 12B:
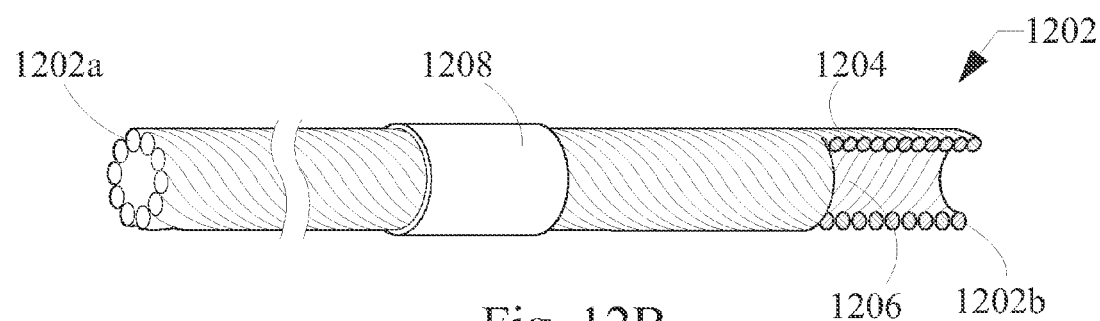

(NOTE: FIGS. 12A-12K, along with all other figures of the present application, may not be drawn to scale). Next, as shown in FIG. 12B, a PEBA barrier sleeve 1208 is placed around a distal region of the shaft wall 1204 and heated to sealingly shrink around it (1204).

Figure 12C:
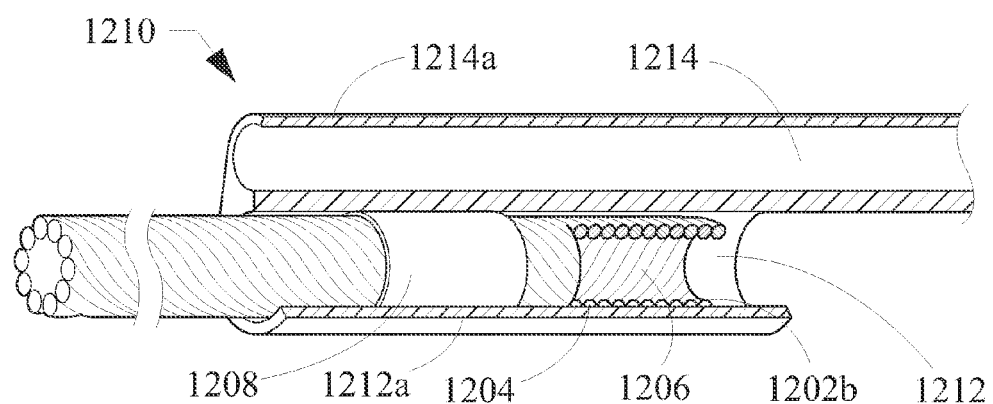

Then, as depicted in FIG. 12C, an elongate dual-lumen sleeve 1210 is provided. The dual-lumen sleeve 1210 includes a lower lumen 1212 and an upper (wire guide) lumen 1214. An upper lumen portion 1214a of the sleeve 1210 extends distally beyond a lower lumen portion 1212a of the sleeve 1210. FIG. 12C shows the dual-lumen sleeve 1210 as having been mounted onto the shaft wall 1204 of the shaft 1202 by sliding a distal portion of the shaft 1202 into the lower lumen 1212 until the distal shaft end 1202b is near the distal end of the lower lumen portion 1212a.

Figure 12D:
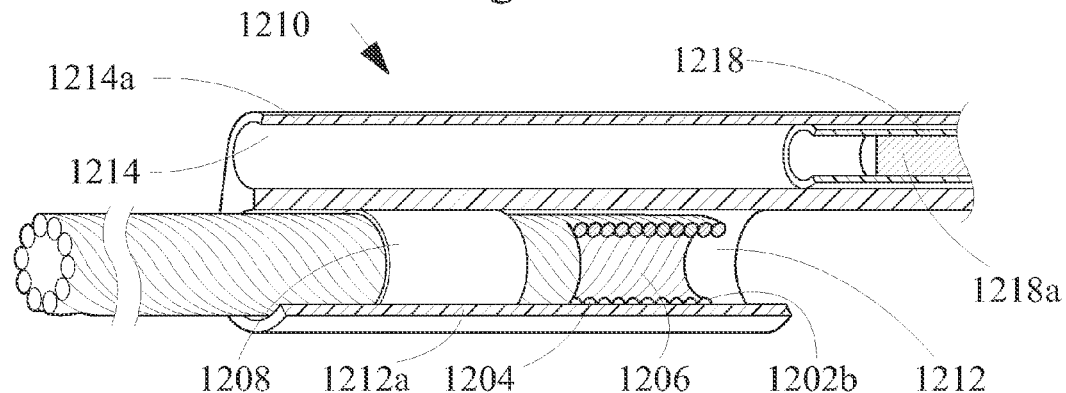
Figure 12E:
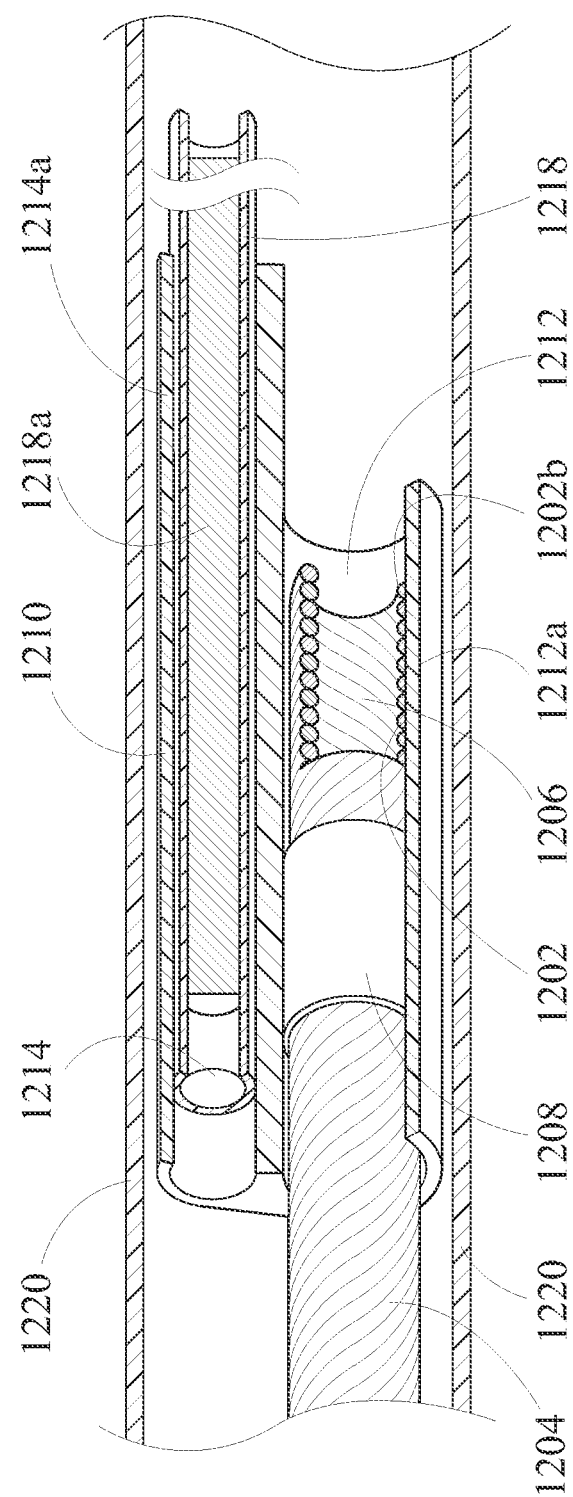
Figure 12F:
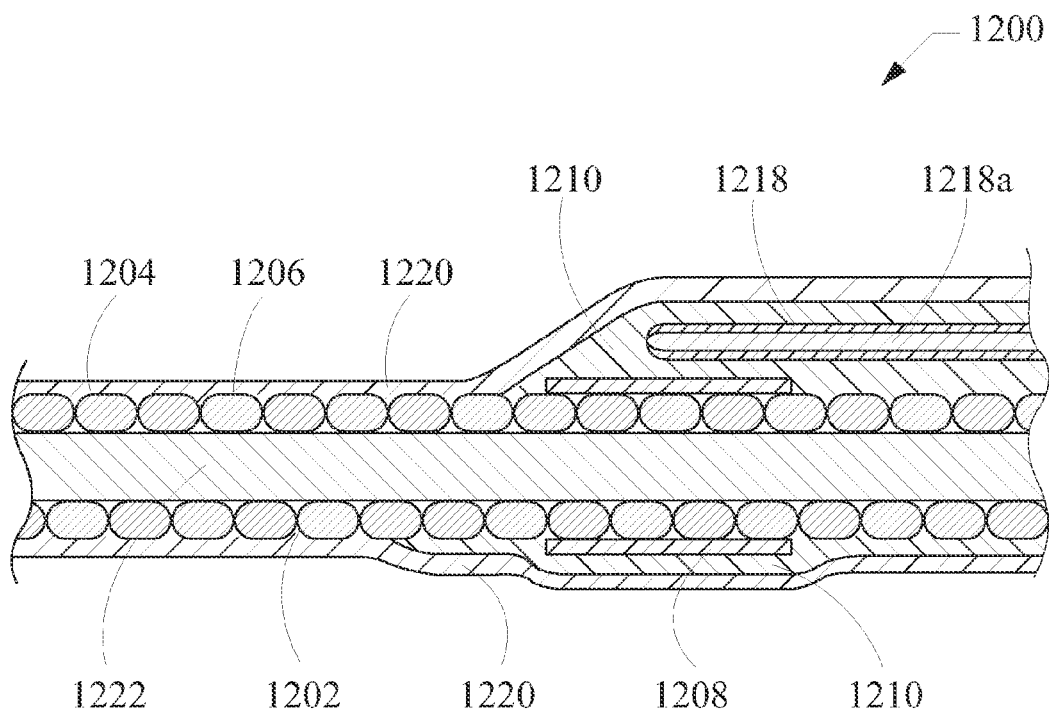

FIG. 12D shows a PTFE wire guide lumen liner 1218 provided on a first mandrel 1218a. The liner 1218 will be directed into the upper (wire guide) lumen 1214 until its (1218) proximal end is adjacent the proximal end of the upper (wire guide) lumen 1214. Next, as shown in FIG. 12E, a tubular PEBA thermoplastic sheath 1220 is directed over the entire length of the shaft 1202 such that it also encircles that portion of the dual-lumen sleeve 1210 around the distal region of the shaft 1202. Then, as illustrated in FIG. 12F, after the assembly is heated, the sheath 1220 shrinks around the shaft length to form a sealing coating 1220 along the length of the shaft 1202 and fusing the dual lumen sleeve 1210 to the shaft wall 1204 and the liner 1218. During the heat-shrink step, a second mandrel 1222 is provided through the shaft lumen 1206 to prevent it from becoming occluded by any coating material that may seep through the shaft wall.

Figure 12G:
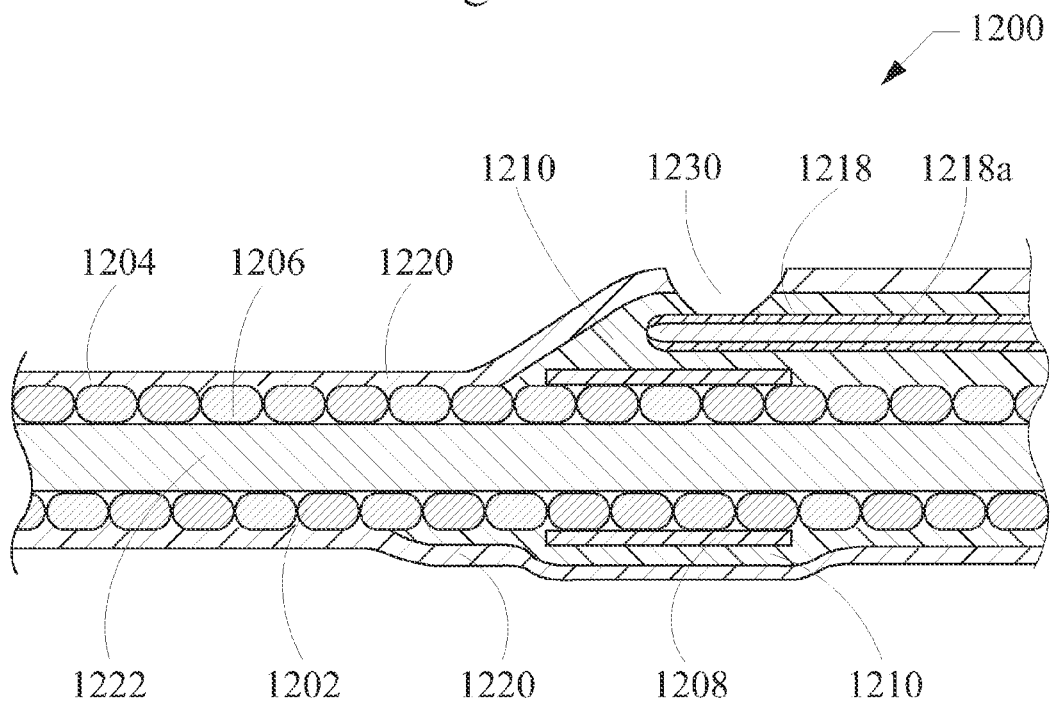
Figure 12H:
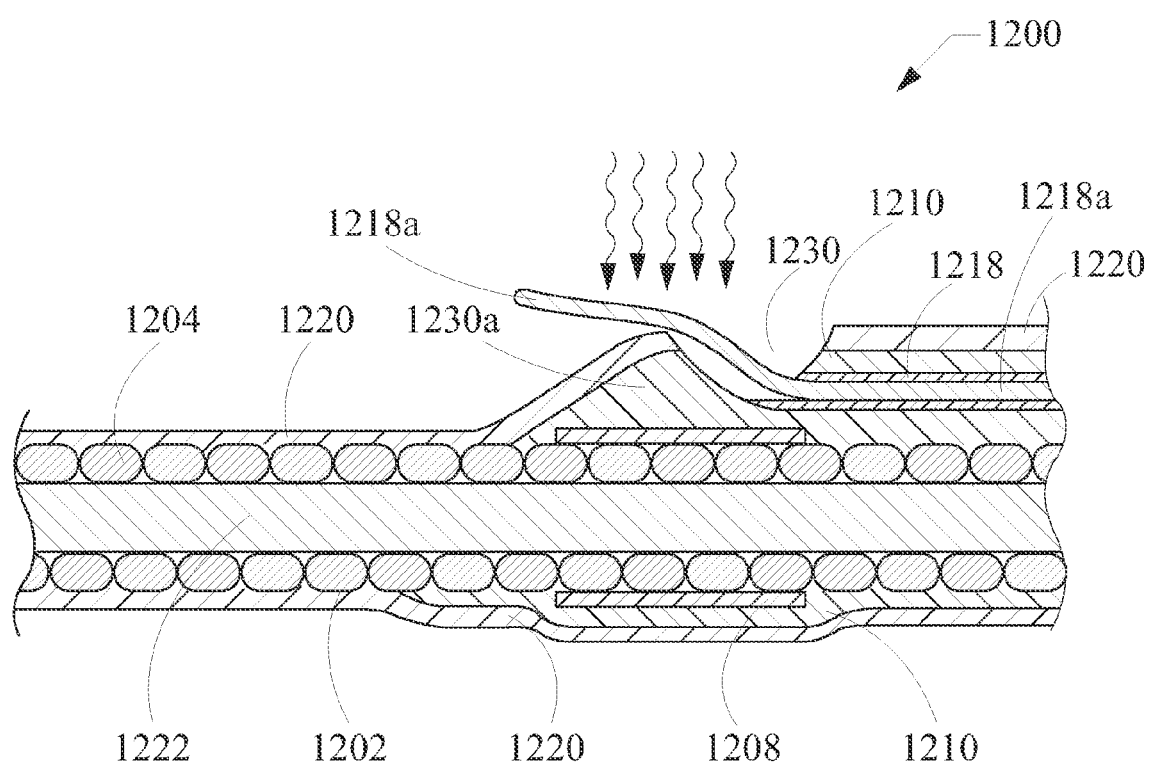

Next, as depicted in FIG. 12G, a wire guide aperture 1230 is skived near the proximal end of the upper (wire guide) lumen 1214 by cutting or otherwise incising through the sheath 1220, the sleeve 1210, and the liner 1218. FIG. 12H shows that the first mandrel 1218a (or a different mandrel, not shown) is directed through the wire guide aperture 1230 in a manner that compresses a portion of the dual lumen sleeve 1210 immediately proximal of the wire guide aperture 1230. The compressed region is heated and, as shown in FIG. 12J, substantially fuses to form a proximal ramped surface 1230a as a proximal portion of the wire guide aperture 1230.

Figure 12K:
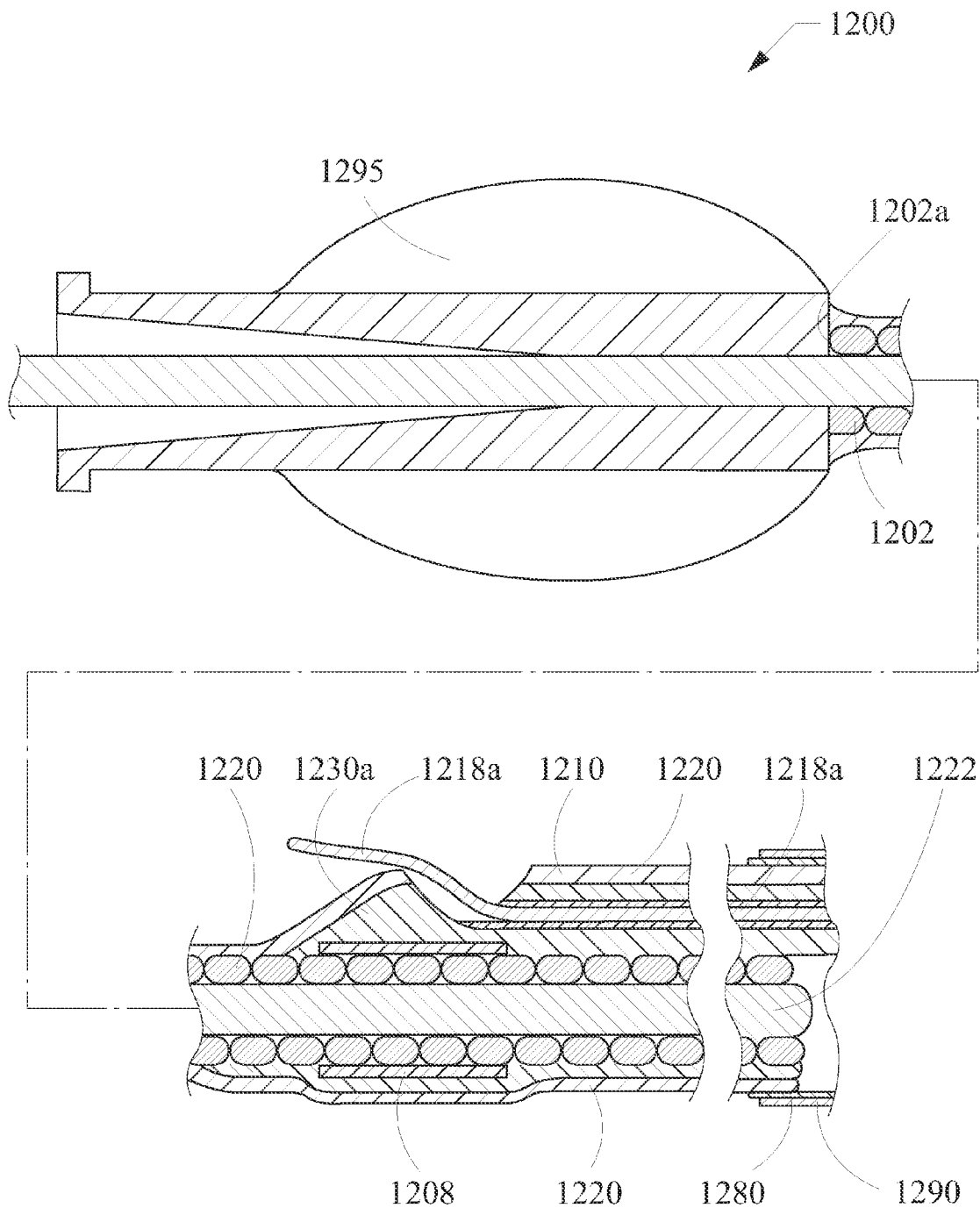

As illustrated in FIG. 12I, the proximal end of a balloon 1280 is attached (preferably by a heat seal or equivalent means) to the assembly adjacent the distal shaft end 1202b such that the upper lumen portion 1214a of the sleeve 1210 extends through the lumen 1282 and distal end of the balloon 1280. The distal end of the balloon 1280 is sealed (also preferably by a heat seal or equivalent means) to the upper lumen portion 1214a of the sleeve 1210, which houses the wire guide lumen 1214. The PTFE wire guide liner 1218 does not need to extend completely to the distal end of the upper lumen portion 1214a of the dual-lumen sleeve 1210. The balloon 1280 can be compressed and folded, and—if desired—a stent 1290 mounted thereto as shown in FIG. 12J. And, as shown in FIG. 12K, a hub 1295 may be mounted to the proximal shaft end 1202a. In another embodiment of this method, the longitudinal shape of that upper lumen portion that is distal of the multifilar shaft may be modified to align generally with a longitudinal axis of that multifilar shaft or of the combined multifilar shaft and outer sleeve 1210 in a manner similar to that shown in FIG. 5C.

In another aspect of the present invention, it should be appreciated that, for the embodiments described above, the multifilar tube may be substituted with a helically-cut or helically-scored hypotube (such as, for example, stainless steel or nitinol hypotube), collectively referred to herein as helically-scored hypotube. Helically-scored hypotube is well known in the catheter art, and those of skill in the art will appreciate that catheter embodiments including a tube of helically-scored hypotube rather than an elongate monolayer multifilar tube may be practiced within the scope of the present invention. For example, one embodiment may include an elongate helically-cut hypotube, said hypotube including a proximal tube end, a distal tube end, and a longitudinal tube lumen extending therebetween. In such an embodiment an inflatable balloon may be disposed adjacent the distal tube end such that a lumen of the balloon is in fluid communication with the longitudinal tube lumen, wherein the tube includes a substantially patent path of fluid communication between a proximal tube portion and the balloon lumen. Such an embodiment may also include a dual-lumen sleeve structure disposed adjacent the distal tube end, said dual-lumen sleeve structure comprising a first sleeve lumen and a second sleeve lumen, wherein the first sleeve lumen includes a wire guide lumen and extends distally beyond the distal tube end. The second sleeve lumen includes a tube-bonding lumen through which is disposed a tube portion adjacent the distal tube end. A coating may be provided that covers substantially the exterior surfaces of the tube and the sleeve structure, and provides a patent fluid communication path along the tube lumen between the proximal tube end and the balloon lumen. In particular, the balloon is connected near its proximal end to the tube and to the sleeve structure, and is also connected distally to the sleeve structure such that at least a portion of the sleeve structure extends through the balloon lumen. In this manner the first sleeve lumen extends distally beyond a distal end of the balloon. Furthermore, a wire guide aperture may be proximally disposed on the wire guide lumen and be configured to provide passage therethrough for a wire guide. Additionally, a wire guide lumen-lining layer may be provided in the wire guide lumen. Also, a sleeve structure may be provided around the hypotube adjacent the wire guide aperture in order, for example, to provide enhanced structural strength and to decrease the likelihood that inflation fluid may travel from the tube lumen to the wire guide lumen. This embodiment may also be used with a stent or other expandable device. Those of skill in the art will note that this embodiment may be understood and practiced, including a method of making the embodiment, with reference to FIGS. 11-12K, wherein helically-cut hypotube is used rather than a multifilar tube, and that other embodiments described above may similarly be adapted for use with helically-cut hypotube within the scope of the present invention.

Those of skill in the art will appreciate that other embodiments and variants of the structures and methods described above may be practiced within the scope of the present invention. It is therefore intended that the foregoing detailed description be regarded as illustrative rather than limiting, and that it be understood that it is the following claims, including all equivalents, that are intended to define the spirit and scope of this invention.

I claim:

1. A medical balloon catheter device configured for use with a wire guide, the catheter comprising:
   an elongate monolayer multifilar tube comprising a plurality of generally longitudinally parallel wires twisted together having a longitudinal central lumen, said tube comprising a length from a proximal tube end to a distal tube end, wherein the longitudinal central lumen has a substantially constant inner diameter along substantially the entire multifilar tube length and extending from the proximal tube end to the distal tube end;
   an inflatable balloon comprising an expandable balloon lumen attached near the distal tube end such that the expandable balloon lumen is in fluid communication with the longitudinal central lumen and the distal tube end extends to the expandable balloon lumen; and
   a dual-lumen sleeve extending proximally from and contacting a proximal portion of the balloon, the dual-lumen sleeve constructed as a continuously integral figure-eight cross-section for at least a lengthwise portion thereof, where the dual-lumen sleeve includes
      a first sleeve lumen configured as a tube-surrounding lumen through which a distal portion of the multifilar tube is disposed and
      a second sleeve lumen constructed as a wire guide lumen structure comprising a longitudinal wire guide lumen, the wire guide lumen structure being disposed adjacent and wholly external of the distal tube end and extending distally beyond the distal tube end, a proximal end of the wire guide lumen structure comprising an aperture open to a proximal end of the wire guide lumen, said aperture configured to allow passage of a wire guide therethrough;
   wherein the dual lumen sleeve substantially prevents fluid communication between the longitudinal central lumen and the wire guide lumen;
   wherein the tube is configured such that a coated proximal tube portion provides a substantially patent path of fluid communication between the proximal tube end and the expandable balloon lumen; and
   wherein the tube further comprises a barrier sleeve around its outer circumference along a lengthwise region immediately adjacent the aperture of the wire guide lumen structure, said barrier sleeve configured to prevent fluid communication between the longitudinal central lumen and the wire guide lumen.

2. The catheter device of claim 1, wherein the wire guide lumen structure extends through an entire length of the expandable balloon lumen.

3. The catheter device of claim 1, wherein a coating of the coated proximal tube portion comprises a material selected from HDPE, PTFE, PET, polyester block amide, polyether block amide, polyurethane, polyimide, polyolefin, nylon, and any combination thereof.

4. The catheter device of claim 1, wherein the barrier sleeve comprises a polymer sheath disposed around a distal portion of the tube.

5. The catheter device of claim 1, wherein the tube-surrounding lumen is bonded to an exterior distal portion of the tube.

6. The catheter device of claim 1, wherein a distal end portion of the balloon is sealed to the wire guide lumen structure to form a fluid-tight seal.

7. The catheter device of claim 1, wherein the wire guide lumen further comprises a lining layer coaxially disposed against a surface of the wire guide lumen.

8. The catheter device of claim 7, wherein the lining layer comprises PTFE.

9. The catheter device of claim 7, wherein the lining is configured to prevent cross-lumen fluid communication.

10. The catheter device of claim 7, wherein the lining is configured to prevent cross-lumen fluid communication between the longitudinal central lumen and the wire guide lumen.

11. The catheter device of claim 7, wherein the lining is configured to prevent cross-lumen fluid communication between the expandable balloon lumen and the wire guide lumen.

12. The medical balloon catheter of claim 1, further comprising a balloon-deployable stent configured to be deployed from the balloon.

13. A medical balloon catheter device configured for use with a wire guide, the catheter comprising:
- an elongate monolayer multifilar tube comprising a plurality of generally longitudinally parallel wires twisted together having a longitudinal central lumen, said tube comprising a proximal tube end and a distal tube end, wherein the longitudinal central lumen extends from the proximal tube end to the distal tube end, said longitudinal central lumen having a substantially constant inner diameter along its entire length;
- a dual-lumen sleeve structure disposed adjacent the distal tube end, said dual-lumen sleeve structure constructed as a continuously integral figure-eight cross-section for at least a lengthwise portion thereof, where the dual-lumen sleeve structure defines a first sleeve lumen and a second sleeve lumen; and
- an inflatable balloon comprising an expandable balloon lumen, said expandable balloon lumen being in fluid communication with the longitudinal central lumen, which longitudinal central lumen extends to the distal tube end at a proximal end of the expandable balloon lumen;
- wherein the first sleeve lumen comprises a wire guide lumen that is disposed adjacent and wholly external of the distal tube end, and that extends distally beyond the distal tube end;
- wherein the second sleeve lumen comprises a tube-bonding lumen through which is disposed a lengthwise multifilar tube portion adjacent the distal tube end;
- wherein a coating covers substantially the exterior surface of the tube and the exterior surface of the sleeve structure, and said coating provides a patent fluid communication path along the longitudinal central lumen between the proximal tube end and the expandable balloon lumen;
- wherein a proximal portion of the balloon is connected to the tube and to the sleeve structure, and is connected distally to the sleeve structure such that at least a portion of the sleeve structure extends through the expandable balloon lumen;
- wherein the first sleeve lumen extends distally beyond a distal end of the balloon;
- wherein a wire guide aperture is disposed on a proximal portion of the wire guide lumen and is configured to provide passage therethrough for a wire guide; and
- wherein the tube further comprises a barrier sleeve around an outer circumference thereof, such that the barrier sleeve is disposed between the tube exterior and the second sleeve lumen along a lengthwise region immediately adjacent the wire guide aperture.

14. The catheter device of claim 13, wherein the coating comprises a material selected from HDPE, PTFE, PET, polyester block amide, polyether block amide, polyurethane, polyimide, polyolefin, nylon, and any combination thereof.

15. The catheter device of claim 13, wherein the wire guide lumen further comprises a lining layer coaxially disposed against a surface of the wire guide lumen.

16. The catheter device of claim 13, further comprising a balloon-deployable stent configured to be deployed from the balloon.

17. A method of making a balloon catheter device comprising the steps of:
- providing an elongate multifilar tube comprising a plurality of generally longitudinally parallel wires twisted together having a longitudinal central lumen, said tube having a proximal tube end and a distal tube end with the longitudinal central lumen extending from the proximal tube end to the distal tube end, said longitudinal central lumen having a substantially constant inner diameter along its entire length;
- providing a dual-lumen sleeve constructed as a continuously integral figure-eight cross-section for at least a lengthwise portion thereof, where the dual-lumen sleeve structure defines an upper sleeve lumen and a lower sleeve lumen, wherein said upper lumen includes a greater distal length than said lower lumen;
- providing a barrier sleeve around an outer circumference of the tube near the distal tube end;
- directing the distal tube end into the lower lumen until the distal tube end is near a distal end of the lower lumen;
- directing a tubular sheath over the tube and the sleeve such that at least a substantial longitudinal portion of the tube and of the sleeve both extend through a sheath lumen of the tubular sheath;
- shrinking the sheath around the tube and sleeve such that the sheath forms a coating thereabout;
- skiving a wire guide aperture into a proximal portion of the upper lumen immediately adjacent the barrier sleeve disposed around the tube;
- providing a balloon having an expandable balloon lumen; and
- attaching the balloon to the tube such that the distal tube end extends at least to the expandable balloon lumen such that the longitudinal central lumen is in fluid communication with the expandable balloon lumen.

18. The method of claim 17, further comprising a step of providing a tubular liner in the upper lumen of the dual-lumen sleeve.

19. The method of claim 17, further comprising a step of providing a mandrel directed through the wire guide aperture and compressing a region immediately proximal thereof to form a ramped surface.

20. The method of claim 17, wherein a portion of the upper lumen that includes the greater distal length than the lower lumen extends through a portion of the expandable balloon lumen.

21. A medical balloon catheter device configured for use with a wire guide, the catheter comprising:
- an elongate tube selected from a monolayer multifilar tube comprising a plurality of generally longitudinally parallel wires twisted together having a longitudinal central lumen and a helically-cut hypotube, said tube comprising a proximal tube end and a distal tube end, the longitudinal central lumen extending from the proximal tube end to the distal tube end, said longitudinal central lumen having a substantially constant inner diameter along its entire length;
- a dual-lumen sleeve structure disposed adjacent the distal tube end, said dual-lumen sleeve structure constructed as a continuously integral figure-eight cross-section for at least a lengthwise portion thereof, where the dual-lumen sleeve structure includes a first sleeve lumen and a second sleeve lumen; and
- an inflatable balloon comprising an expandable balloon lumen, said expandable balloon lumen being in fluid communication with the longitudinal central lumen, which longitudinal central lumen extends to the distal tube end at a proximal end of the expandable balloon lumen;

wherein the first sleeve lumen comprises a wire guide lumen that is disposed adjacent and wholly external of the distal tube end, and that extends distally beyond the distal tube end;

wherein the second sleeve lumen comprises a tube-bonding lumen through which is disposed a lengthwise tube portion adjacent the distal tube end;

wherein a coating covers substantially the exterior of the tube and the exterior surface of the sleeve structure, and said coating provides a patent fluid communication path along the longitudinal central lumen between the proximal tube end and the expandable balloon lumen;

wherein a proximal portion of the balloon is connected to the tube and to the sleeve structure, and is connected distally to the sleeve structure such that at least a portion of the sleeve structure extends through the expandable balloon lumen;

wherein the first sleeve lumen extends distally beyond a distal end of the balloon;

wherein a wire guide aperture is disposed on a proximal portion of the wire guide lumen and is configured to provide passage therethrough for a wire guide; and wherein the tube further comprises a barrier sleeve around an outer circumference thereof, such that the barrier sleeve is disposed between the tube exterior and the second sleeve lumen along a lengthwise region immediately adjacent the wire guide aperture.

22. The medical balloon catheter device of claim 21, wherein the elongate tube is a helically-cut hypotube.

* * * * *

UNITED STATES PATENT AND TRADEMARK OFFICE
CERTIFICATE OF CORRECTION

| | | |
|---|---|---|
| PATENT NO. | : 8,657,845 B2 | Page 1 of 1 |
| APPLICATION NO. | : 11/748906 | |
| DATED | : February 25, 2014 | |
| INVENTOR(S) | : David Christian Lentz | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1041 days.

Signed and Sealed this
Twelfth Day of May, 2015

Michelle K. Lee
*Director of the United States Patent and Trademark Office*